United States Patent
Machida et al.

(10) Patent No.: US 11,914,918 B2
(45) Date of Patent: Feb. 27, 2024

(54) MEDICAL INFORMATION PROCESSING APPARATUS, MEDICAL INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventors: Yoshihito Machida, Kanagawa (JP); Yoshinori Hirano, Chiba (JP); Hideaki Miyamoto, Tokyo (JP); Daisuke Yamada, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 513 days.

(21) Appl. No.: 17/163,888

(22) Filed: Feb. 1, 2021

(65) Prior Publication Data
US 2021/0158105 A1   May 27, 2021

Related U.S. Application Data

(63) Continuation of application No. PCT/JP2019/026009, filed on Jul. 1, 2019.

(30) Foreign Application Priority Data

Aug. 14, 2018 (JP) ................. 2018-152720

(51) Int. Cl.
G06F 3/14 (2006.01)
G06F 18/214 (2023.01)
(Continued)

(52) U.S. Cl.
CPC ............... *G06F 3/147* (2013.01); *G06F 3/14* (2013.01); *G06F 18/214* (2023.01);
(Continued)

(58) Field of Classification Search
None
See application file for complete search history.

(56) References Cited

U.S. PATENT DOCUMENTS

2012/0197827 A1* 8/2012 Mineno ............... G06N 20/10
706/12
2015/0379432 A1* 12/2015 Ando ..................... G16H 50/20
706/14

(Continued)

FOREIGN PATENT DOCUMENTS

JP   H04-261649 A   9/1992
JP   2011-059810 A   3/2011
(Continued)

OTHER PUBLICATIONS

Notice of Reasons for Refusal issued in corresponding JP Patent Application No. 2018-152719, dated Apr. 3, 2023, pp. 1-10, with English translation.

(Continued)

*Primary Examiner* — Mohammed Rachedine
(74) *Attorney, Agent, or Firm* — Carter, DeLuca & Farrell LLP

(57) ABSTRACT

A medical information processing apparatus comprises an obtaining unit that obtains medical information, a learning unit that performs learning on a function of the medical information processing apparatus using the medical information, an evaluation data holding unit that holds evaluation data in which a correct answer to be obtained by executing the function is known, the evaluation data being for evaluating a learning result of the learning unit, an evaluating unit that evaluates a learning result obtained through learning, based on the evaluation data, and an accepting unit that accepts an instruction to apply a learning result of the learning unit to the function.

20 Claims, 13 Drawing Sheets

(51) Int. Cl.

| | | |
|---|---|---|
| *G06F 18/21* | (2023.01) | |
| *G06F 18/40* | (2023.01) | |
| *G09G 5/14* | (2006.01) | |
| *G06F 3/147* | (2006.01) | |
| *G16H 50/20* | (2018.01) | |
| *G16H 30/40* | (2018.01) | |
| *G06V 10/774* | (2022.01) | |
| *G06V 10/778* | (2022.01) | |
| *G06V 10/94* | (2022.01) | |

(52) U.S. Cl.
CPC .......... *G06F 18/2178* (2023.01); *G06F 18/40* (2023.01); *G06V 10/774* (2022.01); *G06V 10/7784* (2022.01); *G06V 10/945* (2022.01); *G16H 30/40* (2018.01); *G16H 50/20* (2018.01); *G06V 2201/03* (2022.01)

(56) References Cited

U.S. PATENT DOCUMENTS

| | | | | |
|---|---|---|---|---|
| 2017/0351972 | A1* | 12/2017 | Kaniwa | ............... G06F 30/20 |
| 2018/0150675 | A1* | 5/2018 | Kamiyama | ............ A61B 5/00 |
| 2019/0076108 | A1 | 3/2019 | Machida | |
| 2020/0236303 | A1 | 7/2020 | Machida | |

FOREIGN PATENT DOCUMENTS

| | | | | |
|---|---|---|---|---|
| JP | 2011-212094 A | | 10/2011 | |
| JP | 2012-159886 A | | 8/2012 | |
| JP | 2016-198197 A | | 12/2016 | |
| JP | 2016198197 A | * | 12/2016 | |
| JP | 2017-185007 A | | 10/2017 | |
| JP | 2017-215828 A | | 12/2017 | |
| JP | 2017215828 A | * | 12/2017 | ............. G06F 30/20 |
| WO | 2014/155690 A1 | | 10/2014 | |
| WO | 2017/017722 A1 | | 2/2017 | |
| WO | 2018/070285 A1 | | 4/2018 | |
| WO | WO-2018120426 A1 | * | 7/2018 | ........... G06K 9/6223 |
| WO | WO-2019150813 A1 | * | 8/2019 | ........... G06K 9/6254 |

OTHER PUBLICATIONS

Morita, M., "Simultaneous Segmentation of Multiple Organs Using Data Items of First Layer, Information Processing" Information Processing Society of Japan, IPSJ SIG Technical Report (May 2014) vol. 2014-CVIM-192, No. 16, with English abstract.

Notice of Reasons for Refusal issued in corresponding JP Patent Application No. 2018-152719, dated Oct. 3, 2022, pp. 1-6, with English translation.

International Search Report issued in International Application No. PCT/JP2019/026009 dated Sep. 24, 2019, pp. 1-2, English Translation.

Ishii, T., et al., "Analysis on generic object recognition technique using Conventional Neural Network" Information Processing Society of Japan Technical Report (May 2014) pp. 1-8, vol. 2014-CVIM-192 No. 14.

Yanase, M., et al., "Proposal of Visual Recognition System based on Machine Learning Method" The Papers of Technical Meeting on Information Oriented Industrial System, IEE Japan (May 2014) pp. 1-8.

* cited by examiner

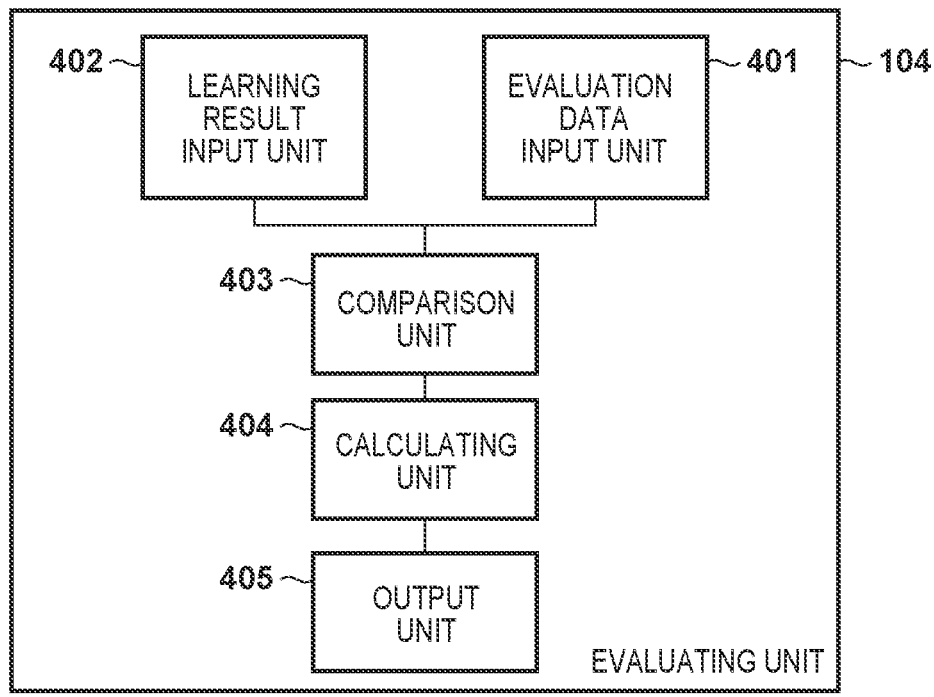
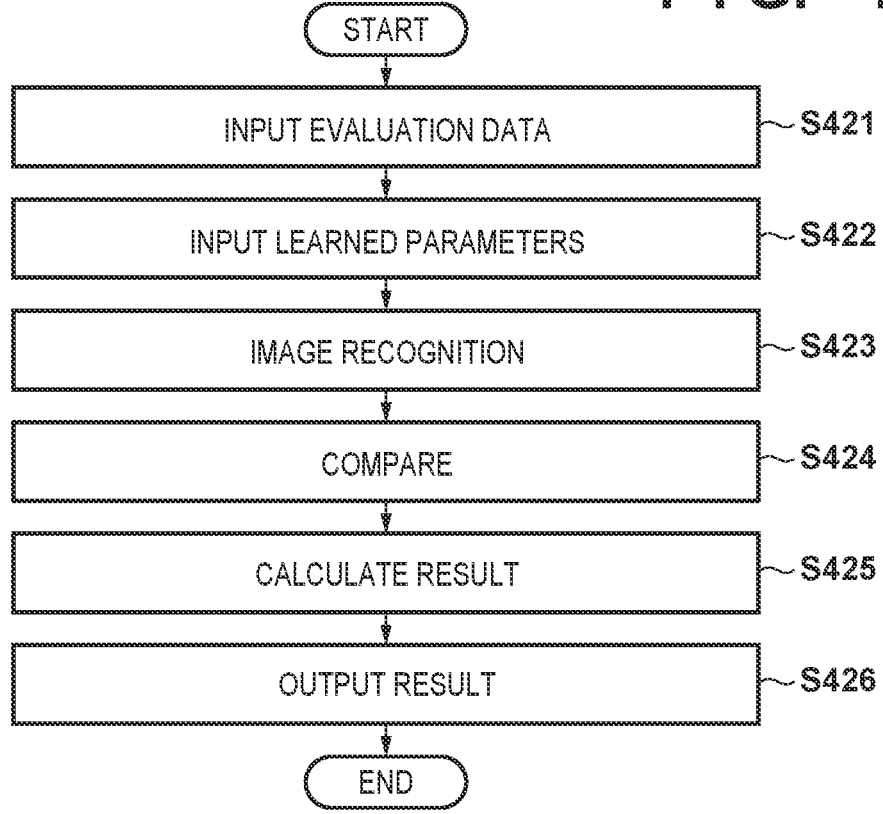

F I G. 5

MEDICAL INFORMATION PROCESSING APPARATUS, MEDICAL INFORMATION PROCESSING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2019/026009, filed. Jul. 1, 2019, which claims the benefit of Japanese Patent Application No. 2018-152720, filed Aug. 14, 2018, both of which are hereby incorporated by reference herein in their entirety.

BACKGROUND OF THE INVENTION

Field of the Invention

The present invention relates to a medical information processing apparatus, a medical information processing method thereof, and a non-transitory computer-readable storage medium.

Background Art

A function of providing information that suits a user's tendency and taste using machine learning, a function of improving the image analysis accuracy, and the like, in medical information processing apparatuses, have been suggested. Patent Document 1 describes a method for improving the image recognition accuracy through machine learning, and detecting a target object. Also, Patent Document 2 describes a method for recognizing a division pattern, an irradiation field, an imaging posture, and an imaging part of a radiation image, using a neural network.

CITATION LIST

Patent Literature

PTL1: Japanese Patent Laid-Open No. 2017-185007
PTL2: Japanese Patent Laid-Open No. H04-261649

Non Patent Literature

NPL 1: Analysis on generic object recognition technique using Conventional Neural Network, Information Processing Society of Japan Technical Report Vol. 2014-CVIM-192 No. 14 (to be referenced in embodiments)

There has been no proposal with regards to validity examination for examining whether or not performance required for achieving an intended use, which is a user's clinical requirement, is met when performance is changed using the above-described machine learning, nor a configuration for the user to easily perform determination on the validity.

SUMMARY OF THE INVENTION

According to one mode of the present invention, a technique for enabling the user to appropriately determine whether or not a learning result can be applied, based on a result of examining the validity of learning is provided.

A medical information processing apparatus according to one mode of the present invention includes the following configuration.

According to one aspect of the present invention, there is provided a medical information processing apparatus comprising: an obtaining unit configured to obtain medical information, a learning unit configured to perform learning on a function of the medical information processing apparatus using the medical information, an evaluation data holding unit configured to hold evaluation data in which a correct answer to be obtained by executing the function is known, the evaluation data being for evaluating a learning result of the learning unit, an evaluating unit configured to evaluate a learning result obtained through learning, based on the evaluation data, and an accepting unit configured to accept an instruction to apply a learning result of the learning unit to the function.

Further features of the present invention will become apparent from the following description of exemplary embodiments with reference to the attached drawings.

BRIEF DESCRIPTION OF THE DRAWINGS

FIG. 4A is a diagram showing an exemplary function configuration of an evaluating unit according to the first embodiment.

FIG. 4B is a flowchart showing the processing procedure of the evaluating unit according to the first embodiment.

FIG. 5 is a diagram showing an example of the difference between a correct answer for an irradiation field and a result obtained through learning.

DESCRIPTION OF THE EMBODIMENTS

Embodiments of the present invention will be described below with reference to the accompanying drawings. Note that, in the embodiments, a medical information processing apparatus for a radiation image will be described, but the present invention is also applicable to medical information processing apparatuses that use another modality, such as CT apparatuses, MRI apparatuses, ultrasonic apparatuses, fundus cameras, OCTs, and endoscopes. The present invention is also applicable to a medical information processing apparatus that uses a plurality of types of modalities. Note that, in the embodiments below, the term "radiation" may include α-rays, β-rays, γ-rays, particle beams, cosmic rays, and the like in addition to X-rays.

First Embodiment

Figure 1:
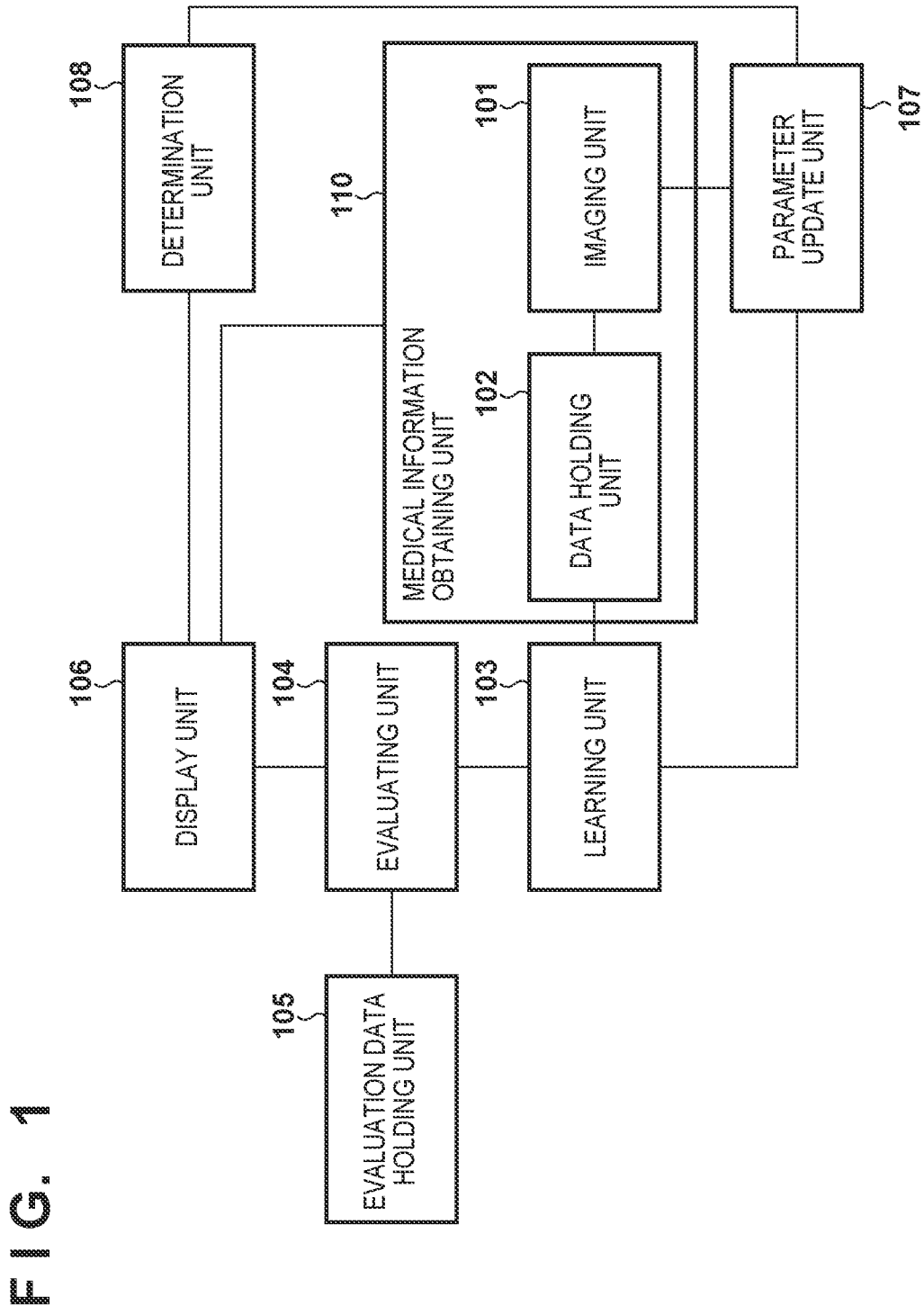
FIG. 1 is a diagram showing an exemplary function configuration of a medical information processing apparatus according to a first embodiment.

FIG. 1 is a block diagram showing an exemplary function configuration of a medical information processing apparatus according to a first embodiment. In a medical information processing apparatus 100, a medical information obtaining unit 110 obtains medical information. A learning unit 103 performs learning for a function of the medical information processing apparatus, using the obtained medical information. An evaluation data holding unit 105 holds evaluation data for evaluating a result of learning performed by the learning unit 103, namely evaluation data in which a correct answer to be obtained by executing the function is known. An evaluating unit 104 evaluates the learning result (learning state) obtained through machine learning performed by the learning unit 103, based on the evaluation data. A display unit 106 functions as a display control unit that causes a display device to display a result of evaluation performed by the evaluating unit 104.

A parameter update unit 107 updates a parameter used by the above function of the medical information processing apparatus, based on the evaluation performed by the evaluating unit 104. A determination unit 108 determines whether or not to update the parameter of the function of the medical information processing apparatus 100 (learning result obtained through machine learning), based on evaluation of learning result. As will be described later, the display unit 106 provides a user interface for displaying the evaluation result and accepting an instruction on whether or not to apply the learning result, and the determination unit 108 determines whether or not to apply the learning result based on an operation on the user interface. In other words, the display unit 106 and the determination unit 108 function as an accepting unit that accepts an instruction to apply the learning result of the learning unit 103 to the function.

In the medical information obtaining unit 110, an imaging unit 101 obtains a medical image to be used as medical information. Examples of the medical image include a radiation image, a CT image, an MRI image, an ultrasonic image, an eye-fundus image, an OCT image, and an endoscope image. In addition, the medical information may include information attached to the medical image (e.g., a tube voltage, an imaging part). The medical information obtaining unit 110 obtains medical information that includes a medical image and information attached to the medical image (hereinafter, attached information), and stores the medical information in a data holding unit 102.

The medical information processing apparatus 100 has a function of image recognition, image processing, diagnosis support, or the like that uses a medical image. When the learning unit 103 performs learning for the function of the medical information processing apparatus 100, the function (the quality of the function) of the medical information processing apparatus 100 changes. For example, if the learning unit 103 performs learning for image recognition that uses a medical image, the accuracy of image recognition changes, if the learning unit 103 performs learning for image processing, the accuracy of image processing changes, or, if the learning unit 103 performs learning for diagnosis support, the accuracy of diagnosis support changes.

The evaluation data holding unit 105 holds evaluation data corresponding to the function of the medical information processing apparatus 100. The evaluation data includes, for example, a medical image that is target data and correct-answer data corresponding to each type of learning (image recognition, image processing, diagnosis support, or the like). Specifically, evaluation data is defined as a medical image and correct-answer data that is known in correspondence with the medical image. For example, evaluation data related to learning for image recognition that uses a medical image includes a medical image that is target data and region information (an irradiation field, an anatomical region, a lesion region, and the like) that is correct-answer data. In addition, for example, evaluation data related to learning for image processing includes a medical image that is target data and image processing conditions (a tone processing condition, a noise processing condition, and the like) that are correct-answer data. In addition, for example, evaluation data related to learning for diagnosis support includes a medical image that is target data and lesion position information that is correct-answer data.

In addition, the evaluation data holding unit 105 may hold evaluation data according to image-capturing mode such as an imaging part, an imaging technique, and the like. For example, the evaluation data holding unit 105 can divide evaluation data to be processed, according to imaging part such as a chest, an abdomen, a head, and four extremities, and hold the evaluation data. For example, the evaluation data holding unit 105 can hold a medical image that is evaluation data and image processing conditions (e.g., a tone processing condition and a noise processing condition) according to imaging part. In addition, for example, the evaluation data holding unit 105 can distinguish evaluation data according to imaging technique such as moving image shooting and still image shooting, and hold the evaluation data. For example, the evaluation data holding unit 105 can hold a medical image that is evaluation data and image processing conditions (e.g., a tone processing condition and a noise processing condition) according to imaging technique.

The evaluating unit 104 analyzes content learned by the learning unit 103 (function of the medical information processing apparatus), reads evaluation data related to the learned content from the evaluation data holding unit 105, and evaluates the learning result. The evaluating unit 104 processes data to be processed included in the evaluation data based on the function in the system using the learning result of the learning unit 103, compares the result with correct-answer data included in the evaluation data, and evaluates the learning result, For example, when evaluating learning for image recognition that uses a medical image, the evaluating unit 104 reads, from the evaluation data holding unit 105, evaluation data related to learning for image recognition that uses a medical image, and evaluates the learning result related to image recognition. In addition, for example, when evaluating learning for image processing that uses a medical image is evaluated, the evaluating unit 104 reads, from the evaluation data holding unit 105, evaluation data related to learning for image processing that uses a medical image, and evaluates the learning result related to image processing. In addition, for example, when evaluating learning for diagnosis support that uses a medical image, the evaluating unit 104 reads, from the evaluation data holding unit 105, evaluation data related to learning for diagnosis support, and evaluates the learning result related to diagnosis support.

Note that, in the above description, evaluation data to be used is selected in accordance with the type of function (type of learning for image recognition, image processing, or diagnosis support), but there is no limitation thereto. For example, a configuration may also be adopted in which the evaluating unit 104 reads evaluation data related to the image-capturing mode when the medical image was obtained, in accordance with image-capturing mode that is based on medical information learned by the learning unit 103, and evaluates the learning result. Examples of the image-capturing mode include imaging parts such as a chest, abdomen, a head, and four extremities as described above. More specifically, when learning for image recognition that uses a medical image of a chest is evaluated, the evaluating unit 104 reads evaluation data from a medical image of a chest, and evaluates the learning result related to image recognition.

Figure 13:
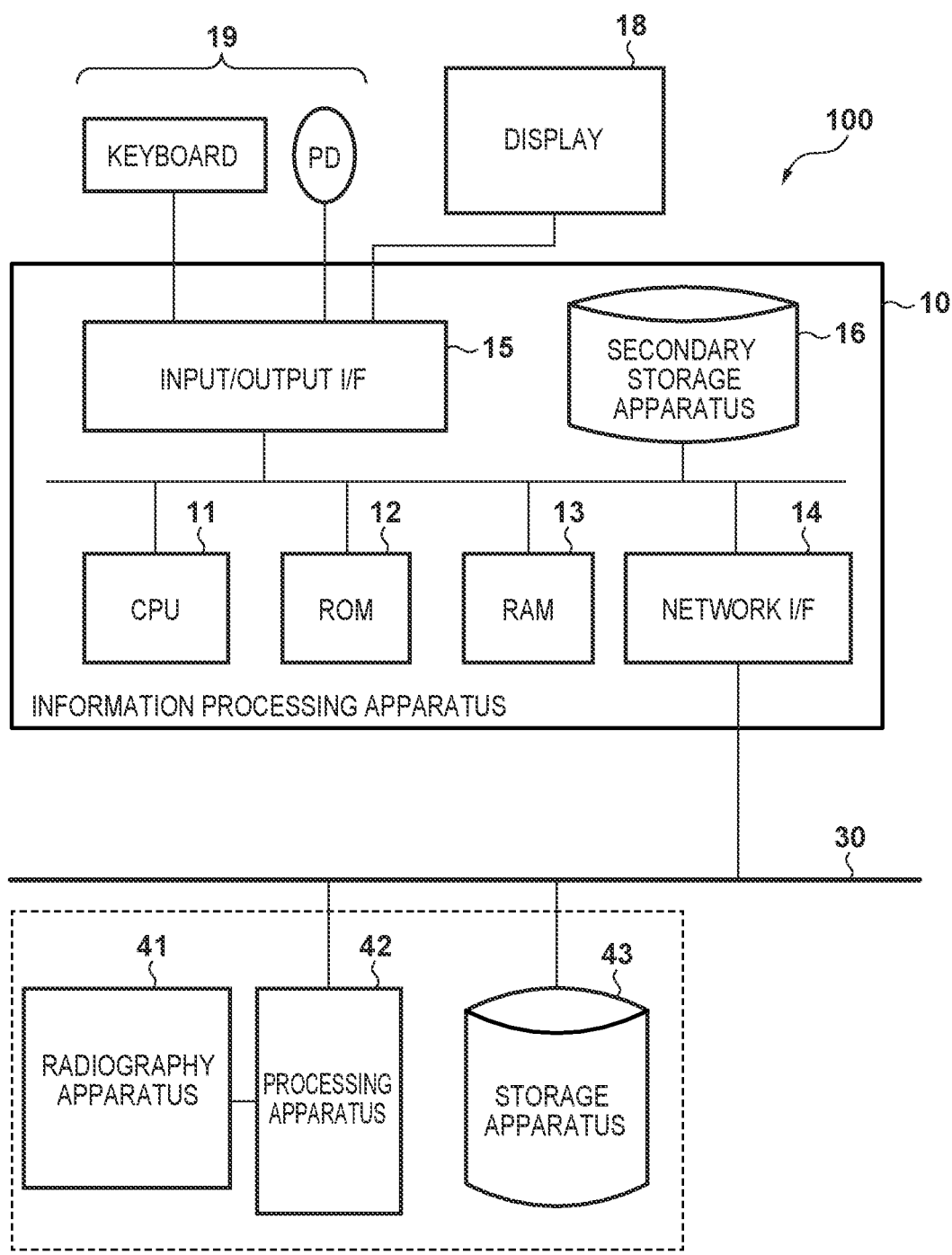
FIG. 13 is a block diagram showing an exemplary hardware configuration of a medical information system according to an embodiment of the present invention.

The display unit 106 executes display control for displaying an evaluation result of a learning result on the display device (for example, a display 18 in FIG. 13). The display unit 106 can also display a medical image. The display unit 106 can display whether the learning result of machine learning (e.g., the accuracy of image recognition, the accuracy of image processing, or the accuracy of diagnosis support) has improved or deteriorated. Specifically, the result of evaluation performed by the evaluating unit 104 is displayed on the display device such that the user can recognize a change due to learning performed by the learning unit 103. The determination unit 108 makes a determination to update the parameter of the function of the medical information processing apparatus in accordance with an instruction from the user after the display unit 106 displays the evaluation result, or automatically based on the learning result. In other words, the determination unit 108 approves the learning result of machine learning performed by the learning unit 103, in accordance with a user's instruction or automatically. If the determination unit 108 made a determination to update the parameter, the parameter update unit 107 updates the parameter that is used by the function of the medical information processing apparatus, using the learning result. In this manner, when the learning result of machine learning performed by the learning unit 103 (e.g., the accuracy of image recognition, the accuracy of image processing, or the accuracy of diagnosis support) improves, the parameter update unit 107 updates the parameter of the function of the medical information processing apparatus.

The determination unit 108 that determines whether or not to update the parameter in accordance with an instruction from the user may be constituted by an approval portion that accepts a user's instruction to approve update of the parameter, and a disapproval portion that accepts a user's instruction to disapprove update of the parameter. For example, the user can view the learning result obtained through machine learning and a medical image, which are being displayed on the display unit 106, and operate the approval portion or the disapproval portion of the determination unit 108. Accordingly, the user can approve or disapprove update of the parameter of the function of the medical information processing apparatus. In addition, a configuration can also be adopted in which, when a learning result obtained through machine learning improves compared with past data, the determination unit 108 automatically makes a determination to update the parameter of the function of the medical information processing apparatus. If the determination unit 108 makes a determination to update the parameter of the function of the medical information processing apparatus, the parameter update unit 107 updates the parameter of the function of the medical information processing apparatus.

FIG. 13 is a block diagram showing an exemplary hardware configuration of the medical information processing apparatus 100 that realizes the above function units.

A radiography apparatus 41 detects radiation emitted from a radiation generation unit (not illustrated), and obtains a radiation image as a medical image. A processing apparatus 42 performs image recognition, image processing, diagnosis support, and the like based on the radiation image obtained by the radiography apparatus 41. The processing apparatus 42 executes the above function of the medical information processing apparatus. A storage apparatus 43 stores a radiation image obtained by the radiography apparatus 41 and attached information of the image, and the radiation image processed by the processing apparatus 42. The processing apparatus 42 and the storage apparatus 43 are connected to a network 30. Note that, the processing apparatus 42 does not need to be an independent apparatus, and, for example, the processing apparatus 42 may also be included in an information processing apparatus 10, or may also be included in the radiography apparatus 41.

In addition, the information processing apparatus 10 is connected to the network 30. In the information processing apparatus 10, a CPU 11 controls the information processing apparatus 10 by executing a program stored in a ROM 12 or a RAM 13, The ROM 12 is a read-only non-volatile memory, and the RAM 13 is an all-time read/write volatile memory. A network I/F 14 connects the information processing apparatus 10 and the network 30. An input/output I/F 15 connects a display 18 and an operation apparatus 19 such as a keyboard and pointing device to the information processing apparatus 10. A secondary storage apparatus 16 is constituted by a hard disk and the like, and stores various types of data and programs. A bus 17 communicably connects the above units.

In the above configuration, for example, the imaging unit 101 can be realized by the radiography apparatus 41 and the processing apparatus 42. Also, the learning unit 103, the evaluating unit 104, the display unit 106, and the parameter update unit 107 can be realized by the CPU 11 executing a predetermined program stored in the ROM 12 or the RAM 13, in the information processing apparatus 10. In addition, the data holding unit 102 may be realized by the processing apparatus 42 using the storage apparatus 43, and the evaluation data holding unit 105 may be realized by the information processing apparatus 10 using the storage apparatus 43.

An example will be described below in which machine learning for improving the accuracy of the function of irradiation field recognition in a radiation image is applied to the medical information processing apparatus 100 according to the first embodiment that has above-described configuration. The imaging unit 101 has a function of detecting radiation that has passed through a subject, and generating a radiation image (the radiography apparatus 41), and an irradiation field recognition function of specifying an irradiation field region from a captured radiation image (the processing apparatus 42).

Figure 2:
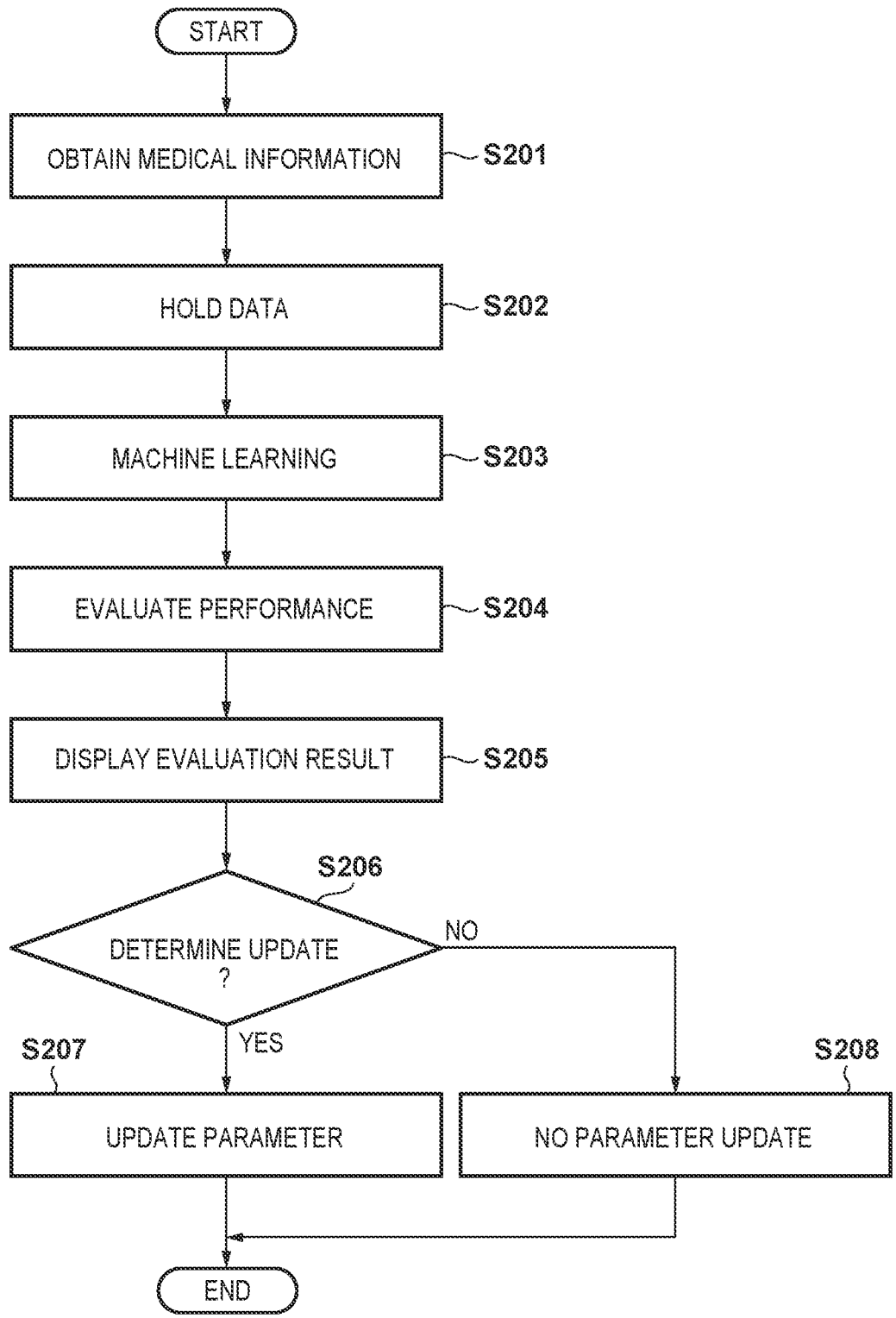
FIG. 2 is a flowchart showing the processing procedure of the medical information processing apparatus according to the first embodiment.

Processing that is performed by the medical information processing apparatus 100 will be described with reference to FIG. 2. FIG. 2 is a flowchart illustrating processing of the medical information processing apparatus 100 according to the first embodiment. In step S201, the imaging unit 101 obtains a radiation image through imaging that uses radiation, and obtains irradiation field information indicating the irradiation field in the radiation image. The irradiation field information is information regarding an irradiated region in a radiation image. The irradiation field information is data in which each coordinate of an irradiation field in a radiation image is set to 0, and each coordinate out of the irradiation field is set to 1, for example. The irradiation field refers to a region in which radiation has reached the imaging unit 101, and a region outside of the irradiation field is a region in which radiation has not reached the imaging unit 101, and that excludes the irradiation field. Reference numeral 501 in FIG. 5 indicates an example of the irradiation field information. The irradiation field information is obtained as a result of the user designating a region or as a result of the user confirming irradiation field information obtained using the irradiation field recognition function (the processing apparatus 42) of the medical information processing apparatus 100, and correcting the irradiation field region as necessary. An algorithm that uses a learning result of a machine learning algorithm is used for the irradiation field recognition function.

In step S202, the data holding unit 102 holds, as medical information, the radiation image and irradiation field information obtained in step S201. In other words, the data holding unit 102 holds a radiation image captured by the imaging unit 101 and information regarding the irradiated region in the radiation image (irradiation field information).

In step S203, the learning unit 103 performs machine learning related to the irradiation field recognition function, using the radiation image and irradiation field information in the data holding unit 102, and obtains a learning result. For example, a Convolution Neural Network (hereinafter, "CNN") described in NPL 1 can be used for machine learning according to this embodiment. Note that the CNN is exemplary, and there is no limitation thereto. For example, the learning unit 103 can use deep learning such as Recurrent Neural Network or Long Short-Term Memory and machine learning such as Support vector Machine or AdaBoost. In addition, a learning result according to this embodiment is represented by parameters such as weights or the like of the layers of the CNN, but the learning result is not limited thereto. For example, a configuration may also be adopted in which a layer configuration or the like is obtained as a learning result.

Figure 3:
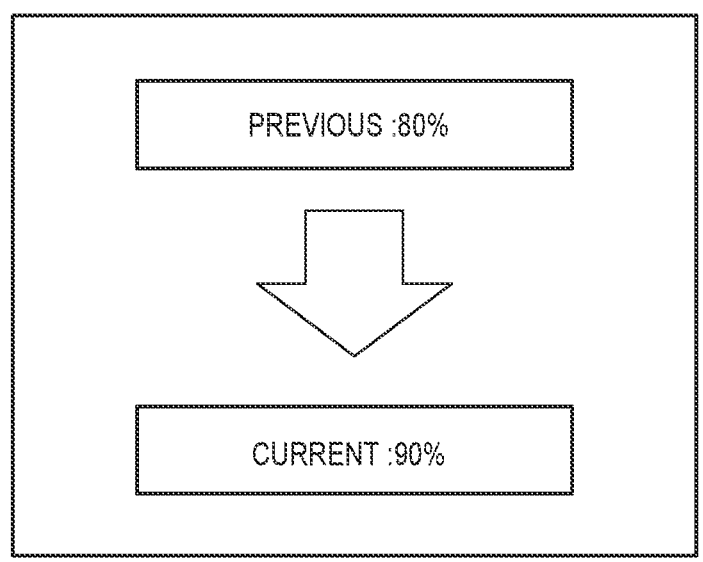
FIG. 3 is a diagram showing a display example of an evaluation result according to the first embodiment.

In step S204, the evaluating unit 104 evaluates the learning result output by the learning unit 103, using evaluation data held in the evaluation data holding unit 105, and obtains an evaluation result. In this embodiment, evaluation data is constituted by a radiation image prepared in advance and irradiation field information thereof (correct-answer data). Note that the evaluation method that is performed by the evaluating unit 104 will be described in detail later. In step S205, the display unit 106 displays the evaluation result obtained by the evaluating unit 104, on a display device. FIG. 3 shows a display example of an evaluation result displayed by the display unit 106. FIG. 3 indicates that the accuracy of irradiation field recognition that is performed using the irradiation field recognition function has improved from 80% to 90%. In other words, the display unit 106 can display whether a learning result of machine learning (the accuracy of irradiation field recognition) has improved or deteriorated.

In step S206, when the determination unit 108 detects that the user confirms the evaluation result and determines that learning is valid, the determination unit 108 makes a determination to cause the parameter update unit 107 to update the parameter of the radiation field recognition function of the imaging unit 101 (learning result obtained through machine learning). In that case, the procedure advances to step S207. On the other hand, when it is detected that the user confirms the evaluation result and determined that learning is not valid, the determination unit 108 makes a determination to not cause the parameter update unit 107 to update the parameter of the radiation field recognition function of the imaging unit 101. In that case, the procedure advances to step S208, Note that the determination unit 108 may automatically determine whether or not the parameter can be updated, based on the evaluation result of the evaluating unit 104. For example, a configuration may also be adopted in which, when the recognition accuracy improves through learning, the determination unit 108 automatically determines that the parameter can be updated. A configuration may also be adopted in which, for example, when the recognition accuracy does not reach a predetermined threshold value, when the improvement rate of the recognition accuracy does not reach a predetermined rate, or when the recognition accuracy deteriorates, the determination unit 108 accepts user's determination, otherwise the determination unit 108 automatically approves update of the parameter.

In step S207, the parameter update unit 107 updates the parameter of the function of the medical information processing apparatus (the radiation field recognition function of the imaging unit 101). In this manner, if the learning result obtained through machine teaming (recognition accuracy of a radiation field region) improves, the parameter update unit 107 updates the parameter of the function of the medical information processing apparatus (the radiation field recognition function of the imaging unit 101). On the other hand, in step S208, the parameter update unit 107 does not update the parameter of the function of the medical information processing apparatus (the radiation field recognition function of the imaging unit 101). In this manner, if the teaming result obtained through machine learning (the recognition accuracy of an irradiation field) deteriorates, the parameter update unit 107 does not updates the parameter of the function of the medical information processing apparatus (the irradiation field recognition function of the imaging unit 101).

As a result of performing the processes in steps S201 to S208 as described above, the validity of machine learning can be examined, and a determination can be made on whether or not the parameter of the function of the medical information processing apparatus can be updated. In addition, in a situation where the function of the medical information processing apparatus may change due to machine learning, an evaluation result after the change is presented to the user, and can be used as a guide when the user makes a determination on the validity. It is possible to examine whether or not performance required for achieving an intended use that is a clinical requirement is satisfied.

Next, the evaluation processing that is performed by the evaluating unit 104 according to the first embodiment will be described in detail with reference to FIGS. 4A and 4B. According to the first embodiment, the validity of a learning result is evaluated using evaluation data that includes a plurality of pairs of image data (radiation images) and irradiation field information of the image data.

FIG. 4A is a block diagram showing an exemplary function configuration of the evaluating unit 104 according to the first embodiment. In the evaluating unit 104, evaluation data is input to an evaluation data input unit 401 from the evaluation data holding unit 105. Learned parameters, which represent a learning result, are input to a learning result input unit 402 from the learning unit 103. A comparison unit 403 compares correct-answer data in the evaluation data with a result obtained by processing the medical image in the evaluation data using the learned parameters. A calculating unit 404 calculates the match rate between the correct-answer data in the evaluation data and the learning data of the learning result. An output unit 405 outputs the result of the calculation performed by the calculating unit 404.

Next, a flow of processing that is executed by the evaluating unit 104 that has the above configuration will be described in detail with reference to FIG. 4B. In step S421, evaluation data is input to the evaluation data input unit 401 from the evaluation data holding unit 105. As described above, according to this embodiment, evaluation data includes image data (medical image) that is target data and irradiation field information serving as correct-answer data (hereinafter, "correct-answer irradiation field"). In step S422, the learned parameters representing a learning result of the learning unit 103 are input to the learning result input unit 402. As described above, according to this embodiment, the parameters are weight coefficients of the layers of the CNN. In step S423, the processing apparatus 42 performs image recognition of the image data included in the evaluation data, based on the learned parameters. According to this embodiment, the processing result is represented by irradiation field information (hereinafter, "learned irradiation field"). In step S424, the comparison unit 403 compares the correct-answer irradiation field with the learned irradiation field, and calculates a match rate.

Figure 5:
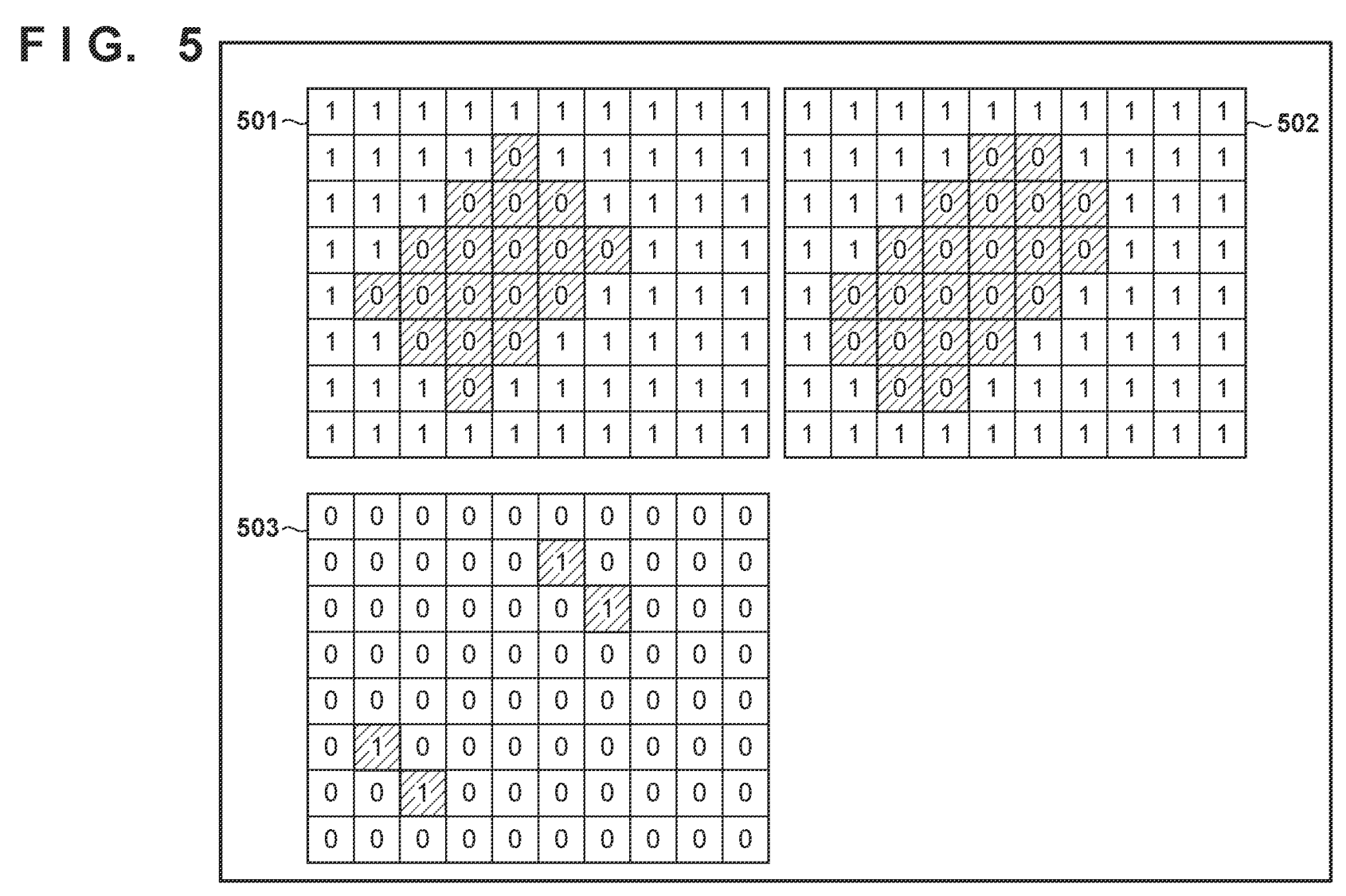

FIG. 5 shows a comparative example of irradiation fields obtained by the comparison unit 403. FIG. 5 shows examples of a correct-answer irradiation field 501, a learned irradiation field 502, and a comparison irradiation field 503. Regarding the correct-answer irradiation field 501 and the learned irradiation field 502, the pixels indicated by "1" are outside of the irradiation field, and pixels indicated by "0" are within the irradiation field. In addition, regarding the comparison irradiation field 503, "0" indicates a pixel in which the correct-answer irradiation field and the learned irradiation field match, and "1" indicates a pixel for which the correct-answer irradiation field and the learned irradiation field do not match. In the example in FIG. 5, 76 pixels out of all of the 80 pixels match, and the match rate in this case is 76/80×100=95%.

Returning to FIG. 4B, in step S425, the calculating unit 404 calculates a result based on all of the comparison results. According to this embodiment, a threshold is provided for the match rate, and recognition accuracy is calculated for all of the comparison results based on a match rate of 95% or higher indicating a correct answer and a match rate of less than 95% indicating a non-correct answer. For example, if 90 examples out of 100 have a match rate of 95% or higher, the recognition accuracy is 90/100×100=90%. In step S426, the output unit 405 outputs the result calculated by the calculating unit 404 to the display unit 106. The user can easily confirm the validity of the learning result updated through machine learning, as a result of the processes in steps S421 to S426 being performed in this manner.

Next, an evaluation display method, a validity examination method, and a parameter update method of the display unit 106 and the parameter update unit 107 will be described in detail with reference to FIG. 6A. The display unit 106 provides, to the user, reference data for performing a determination on whether or not to reflect the learning result, by displaying evaluation results before and after learning is performed by the learning unit 103, the evaluation results having been obtained by the evaluating unit 104.

Figure 6A:
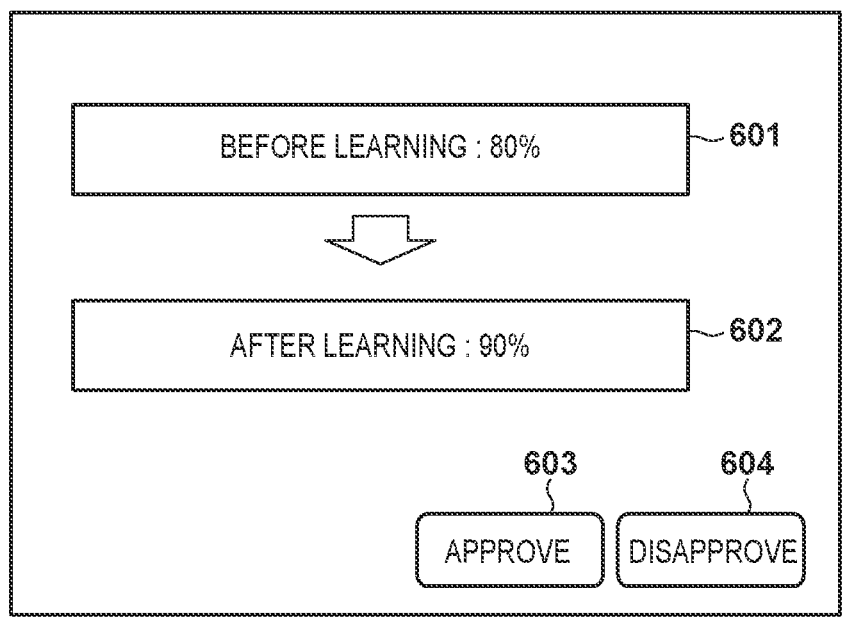
FIG. 6A is a diagram showing an example of display appearance of a display unit according to the first embodiment.

FIG. 6A is a diagram showing a display example of an evaluation result of the display unit 106. Reference numeral 601 indicates an evaluation result before machine learning, and reference numeral 602 indicates an evaluation result after machine learning. Reference numeral 603 indicates an approval portion (approval icon) for approving update of the parameter of the function of the medical information processing apparatus (learning result of machine learning). Reference numeral 604 indicates a disapproval portion (disapproval icon) for disapproving update of the parameter of the function of the medical information processing apparatus. A mode is illustrated in which the approval portion 603 and the disapproval portion 604 of the determination unit 108 are incorporated in the display unit 106. The approval portion 603 and the disapproval portion 604 are examples of a configuration for accepting a user's instruction to apply a learning result of the learning unit 103 to a corresponding function of the medical information processing apparatus. Note that, according to the first embodiment, the evaluation results 601 and 602 each indicate the ratio of evaluation data determined as a correct answer, but may indicate the ratio of evaluation data determined as an incorrect answer.

The display unit 106 displays the evaluation result 601 before machine learning and the evaluation result 602 after machine learning. In this example, the result before machine learning is 80%, and the result after machine learning is 90%. The user confirms the evaluation results before and after machine learning, and presses "the approval portion 603" or "the disapproval portion 604" to select approval or disapproval. When "the approval portion 603" is pressed, the determination unit 108 determines that the user has approved the learning result, and causes the parameter update unit 107 to reflect the learning result on the imaging unit 101. On the other hand, when "the disapproval portion 604" is pressed, the determination unit 108 determines that the user has disapproved the learning result, and does not cause the parameter update unit 107 to reflect the learning result on the imaging unit 101.

As described above, as a result of displaying evaluation results, and the user confirming the evaluation results and performing determination, it is possible to secure the performance of machine learning.

Note that, in this embodiment, an example has been described in which an evaluation result after learning is higher than an evaluation result before learning, but, in actuality, a case is also conceivable in which an evaluation result after learning is lower than an evaluation result before learning. For example, when machine learning is proceeded using data obtained in a facility, a state of being optimized in the facility is envisioned, and thus it is conceivable that a result of evaluation performed using evaluation data prepared in advance will be low. On the other hand, a case is conceivable in which performance has deteriorated due to overlearning or use of incorrect learning data. Even in such a case, for example, the user can determine that learning is valid if the result of evaluation performed using the evaluation data is not lower than a certain baseline. In this manner, a function of displaying evaluation data such that the evaluation data is approved or disapproved is provided, and thereby the user can easily perform validity examination.

Note that, according to the first embodiment, the irradiation field recognition function has been described as an example, but the present invention is applicable to any medical information processing apparatus that uses a machine learning system such as a function of recognizing a region of interest or an imaging part or a function of providing diagnosis support information such as the position and/or the degree of malignancy of a tumor mass. In addition, according to this embodiment, a combination of image data and irradiation field information is used as learning data or evaluation data, but there is no limitation thereto. The present invention is also applicable to any machine learning system that uses, as data, one of image data, diagnostic information, gene information, inspection information of a plurality of modalities, gender, age, and body height, for example.

In addition, in this embodiment, a description has been given on performing machine learning using data obtained by the medical information processing apparatus, but the present invention is also applicable regardless of what system obtained data for performing machine learning. The present invention is also applicable to a medical information processing apparatus that uses a dataset for machine learning that is called public dataset and is publicized on the Internet, for example. In addition, in this embodiment, all of the constituent elements of the medical information processing apparatus 100 do not need to be in the same facility. For example, the medical information processing apparatus may have a configuration in which the imaging unit 101 and the display unit 106 that displays a validity evaluation result are in a hospital, and the other constituent elements are in a cloud.

Variation 1-1

In the first embodiment, functions related to image analysis, for example, region determination such as the radiation region recognition function, and provision of diagnosis support information have been described as functions that use machine learning, but, in this variation, an application example related to preferences in image quality will be described.

Regarding a diagnostic image such as a radiation image, preferences in image quality differ according to a medical practitioner that performs interpretation of radiogram, a medical department, and a facility, and, for example, preferences in contrast, luminance, sharpness, and noise amount vary. In this variation, a method for automatically setting a parameter for improving the image quality in machine learning is envisioned. A learning result is obtained by inputting, as learning data, a captured image and an image adjusted to the optimum image quality by the user, and a parameter for improving the image quality is automatically set. With such a configuration, it is envisioned that an image that is based on preferences is created for various imaging conditions and subjects. In this case, an image captured as evaluation data and an image obtained by adjusting the image to the optimum image quality are used in evaluation, in addition to learning data.

In this case, evaluation is performed by comparing the captured image in the evaluation data with the image to which an image adjustment parameter obtained in the learning result is applied. Image comparison can be performed by using the square of the difference, the difference between maximum values/minimum values/most frequent values of histograms, the difference in standard deviation of a designated region, or the like. The difference value calculated through the above-described evaluation is displayed in the evaluation results 601 and 602, for example. In this manner, according to Variation 1-1, the validity can be examined for not only a function that uses image analysis, but also function that is based on preferences in image quality.

As described above, according to the first embodiment and Variation 1-1 thereof, evaluation is performed using evaluation data that includes target data and correct-answer data. Accordingly, the ratios of evaluation data determined as correct answers or incorrect answers by comparing the correct-answer data with processing results of the target data for the function before and after learning are displayed as evaluation results before and after learning. The user can give an instruction on whether or not the learning result can be reflected, by viewing these evaluation results and operating the approval portion 603 or the disapproval portion 604.

Second Embodiment

In a second embodiment, display of a failure example for the user to efficiently examine the validity will be described. Note that the function configuration, the processing flow, and the hardware configuration are similar to the first embodiment (FIGS. 1, 2, and 13). Mainly, the display appearance of an evaluation result on the display unit 106 is different between the first embodiment and the second embodiment. Similarly to the first embodiment, the evaluating unit 104 obtains the difference between a processing result obtained by processing target data included in evaluation data for a function after learning and correct-answer data included in the evaluation data, and determines whether or not the processing result is an incorrect answer, based on that difference. The display unit 106 according to the second embodiment displays the processing result determined as being an incorrect answer by the evaluating unit 104, on a display device (the display 18) along with target data and correct-answer data of corresponding evaluation data. A specific example of a case Where the target data is a medical image, the correct-answer data is radiation field information, and the function for which learning is performed is the radiation field recognition function will be described below.

Figure 6B:
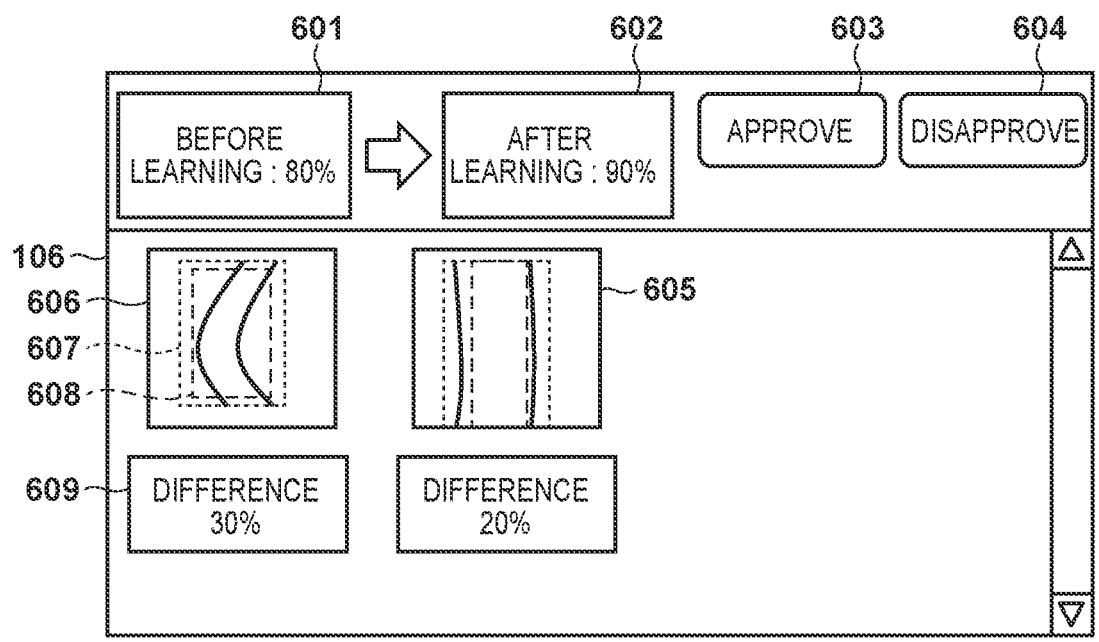
FIG. 6B is a diagram showing an example of display appearance of a display unit according to a second embodiment.

FIG. 6B is a diagram showing a display example of an evaluation result according to the second embodiment. Similarly to the first embodiment (FIG. 6A), the display unit 106 displays the evaluation result 601 before machine learning, the evaluation result 602 after machine learning, the approval portion 603, and the disapproval portion 604. In the illustrated example, the evaluation result 601 before machine learning (correct answer ratio) is 80%, and the evaluation result 602 after machine learning (correct answer ratio) is 90%. The user confirms the evaluation results before and after machine learning, and presses the approval portion 603 or the disapproval portion 604 so as to select approval or disapproval. Here, the correct answer ratio after machine learning is 90%, and thus the remaining 10% is represented by the incorrect answer rate.

According to the second embodiment, the display unit 106 further displays a target medical image determined as being an incorrect answer in evaluation of a learning result performed by the evaluating unit 104, and the cause of it. Specifically, the display unit 106 displays medical images 605 and 606 that are target data of evaluation data determined as incorrect answers, correct-answer data (a boundary 607) of that evaluation data, and a processing result (a boundary 608) for the function for which learning was performed by the learning unit 103. In addition, the display unit 106 displays difference information 609 indicating a difference related to a processing result determined as an incorrect answer.

The user can recognize the difference between the learning result of the learning unit 103 and the correct-answer data by confirming the difference information 609 displayed on the display unit 106. In the above-described example of radiation field recognition, the evaluating unit 104 compares a correct-answer radiation field with a learning radiation field, and calculates the match rate. The evaluating unit 104 calculates the difference (numerical value) based on the calculated match rate. For example, if the match rate is 80%, the difference is 20%, and, if the match rate is 70%, the difference is 30%. The display unit 106 displays information indicating the difference as the difference information 609. The user can recognize the difference between the learning result of the learning unit 103 and the correct-answer data, based on the difference information 609. If the difference indicated in the difference information 609 is large, it is possible to confirm the medical image 606 determined as an incorrect answer, and recognize the difference state.

Furthermore, in the medical image 606, the boundary 607 of the correct-answer radiation field and the boundary 608 of the radiation field, which is a processing result obtained for the function after learning, are displayed. The user can recognize the state of the difference between the correct-answer data of the evaluation data and the processing result obtained for the function after learning, based on the boundary 607 of the correct-answer radiation field and the boundary 608 of the radiation field that is a processing result, the boundaries being displayed in the medical image 606. Accordingly, the user can recognize which boundary is deviated or the degree to which the boundary is deviated, based on the medical image 606, by confirming the boundary 607 of the correct-answer radiation field and the boundary 608 of the radiation field that is the processing result obtained for the function after learning, which are displayed in the medical image 606.

Note that a setting unit (not illustrated) for accepting setting of the range of difference performed by the user may also be provided. The set difference is used for narrowing down a medical image to be displayed on the display unit 106. In other words, the display unit 106 sets, as a display target, a processing result for which the difference obtained by the evaluating unit 104 is within the range set by the user. For example, it is possible to set a difference for narrowing down a medical image to be displayed, within a predetermined range (for example, 30% to 10% or higher). If the range of difference for narrowing down a medical image to be displayed is set to 20%, a medical image for which the difference calculated for the processing result is 20% or higher is displayed on the display unit 106. Similarly, if the difference for narrowing down a medical image to be displayed is set to 30%, a medical image for which the difference is 30% or higher is displayed on the display unit 106. In the example shown in FIG. 6B, the difference for narrowing down a medical image to be displayed is set to 20%, and the medical image 606 for which the difference is 20% and the medical image 605 for which the difference is 30% are displayed on the display unit 106.

In addition, the display unit 106 may display processing results in the order of largest difference, for a plurality of medical images determined as incorrect answers. As shown in FIG. 6B, a processing result (the medical image 606) for which the difference is 30% and a processing result (the medical image 605) for which the difference is 20% are displayed in order from the upper left. With such display appearance, the user can promptly recognize the medical image for which the difference is larger and the cause of it. In addition, the display unit 106 may also display the number of processing results determined as incorrect answers by the evaluating unit 104 (the number of incorrect answers). With such display appearance, if there are a large number of medical images determined as incorrect answers, the user can also recognize the number of medical images that have been determined as incorrect answers and are not displayed on the display unit 106.

In addition, as described above, the display unit 106 displays the difference information 609 along with the evaluation result 601 before machine learning and the evaluation result 602 after machine learning. Thus, if the difference indicated by the difference information 609 is small, even if the evaluation result 602 after machine learning (correct answer ratio) is low, the user can approve the learning result obtained through machine learning performed by the learning unit 103, and update the parameter of the function of the medical information processing apparatus.

In this manner, as a result of a failure example being displayed, the user can confirm a case where the failure has occurred, which is used as information for determination for validity examination. For example, when the evaluation result after leaning exceeds a baseline but there is a failure example that is clinically unacceptable, the user can disapprove the learning as being not valid. On the other hand, when the evaluation result after learning does not exceed the baseline but there is no failure example that is clinically unacceptable, the user can approve the learning as being valid. In this manner, even in a case where the presence or absence of performance required for a clinical practice cannot be determined based only on an evaluation value, the user can examine the validity by failure examples being displayed.

In addition, in this embodiment, an example has been described in which the validity can be confirmed without confirming all the examples, by displaying failure examples only, but the present invention is also applicable to a system that can display not only failure examples, but also correct answer examples. As a result of displaying a correct answer example in this manner, if there is a case of determination as a correct answer in terms of an evaluation value, but needs to be clinically determined as a failure, the user can disapprove the learning as being not valid. In addition, when there is a very large amount of evaluation data and it is difficult to display all of the failure examples, the display unit 106 may pick up representative examples from among those failure examples and display the representative example. Examples of a method for picking up representative examples include picking up a predetermined number of failure examples in the order of largest difference.

Note that, according to the second embodiment, correct-answer data and a processing result are superimposed on a medical image of evaluation data, but display appearance of failure examples is not limited thereto. For example, when learning is performed for a function related to preferences in image quality described in Variation 1-1, correct-answer data is an image processing condition. In this case, it is sufficient that an image obtained by processing a medical image using a learned image processing condition is displayed as a processing result, and a result obtained by processing a medical image based on an image processing condition of correct-answer data is displayed as an image of correct-answer data. This applies to the following variations.

Variation 2-1

Figure 7A:
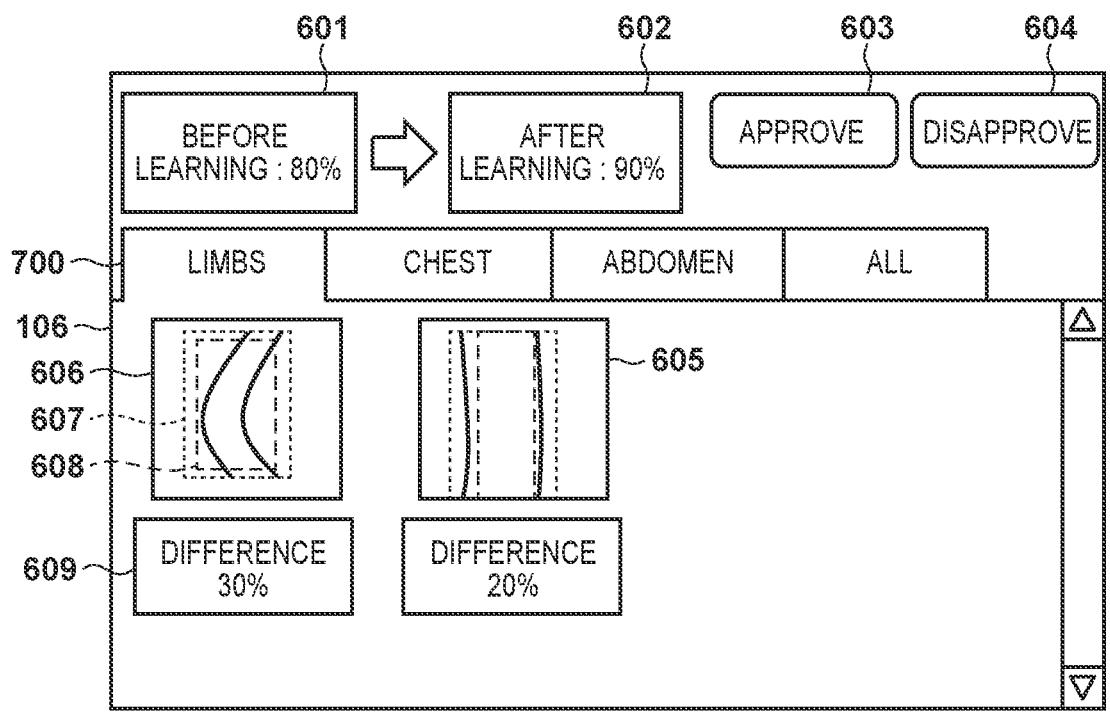
FIG. 7A is a diagram showing a variation of display appearance.

In the second embodiment, an example has been described in which failure examples are displayed, but, in Variation 2-1, a display example will be described in which failure examples are displayed for each site. Specifically, according to Variation 2-1, the display unit 106 displays, for each site, a processing result determined as an incorrect answer by the evaluating unit 104. A detailed description will be given below. FIG. 7A shows a display example of the display unit 106 according to Variation 2-1. The display unit 106 displays, for each site, target medical images determined as incorrect answers in evaluation of a learning result performed by the evaluating unit 104 and the cause for it. Specifically, the display unit 106 displays, for each site, medical images determined as incorrect answers, and difference information indicating the difference between correct-answer data of evaluation data held in the evaluation data holding unit 105 and a learning result of the learning unit 103.

A site selection unit (site selection tag) 700 for selecting a site is displayed on the display unit 106. In this example, one of "four extremities", "chest", "abdomen", and "all" can be selected by using the site selection unit 700. As a result of the user operating the site selection unit 700 and giving an instruction on a site, failure examples for the site are displayed. For example, when the user selects "four extremities" using the site selection unit 700, a medical image of four extremities determined as an incorrect answer in evaluation of a learning result, and the cause of it are displayed. When the user selects "chest" using the site selection unit 700, a medical image of a chest determined as an incorrect answer in evaluation of a learning result, and the cause of it are displayed.

As a result of displaying failure examples for each target site in this manner, each site that the user think is particularly important can be confirmed, and thus the validity can be efficiently examined. For example, in a facility in which only chests are imaged, a result of only a chest can be confirmed by using Variation 2-1.

Note that, according to Variation 2-1, the evaluation result 601 before machine learning, the evaluation result 602 after machine learning, the approval portion 603, and the disapproval portion 604 operate similarly to the second embodiment, but each of them may operate in conjunction with the site selection unit 700. For example, a configuration may be adopted in which, when a chest is selected using the site selection unit 700, an evaluation result for which evaluation data of a chest was used is displayed, and when the approval portion 603 is selected, a learning result for a target function at the time of chest imaging is reflected. As a result of those units operating in conjunction, for example, when performance for chest imaging improves and the user determines that the learning is valid, but determines that the learning is not valid regarding other imaging, performance can be improved only for a chest. In addition, regarding picking up of a failure example described in the second embodiment, the user can confirm a failure example evenly in terms of sites by picking up a failure example for each site.

Variation 2-2

According to Variation 2-2, the display unit 106 displays a processing result determined as an incorrect answer by the evaluating unit 104, for each type of learned function. A detailed description will be given below.

Figure 7B:
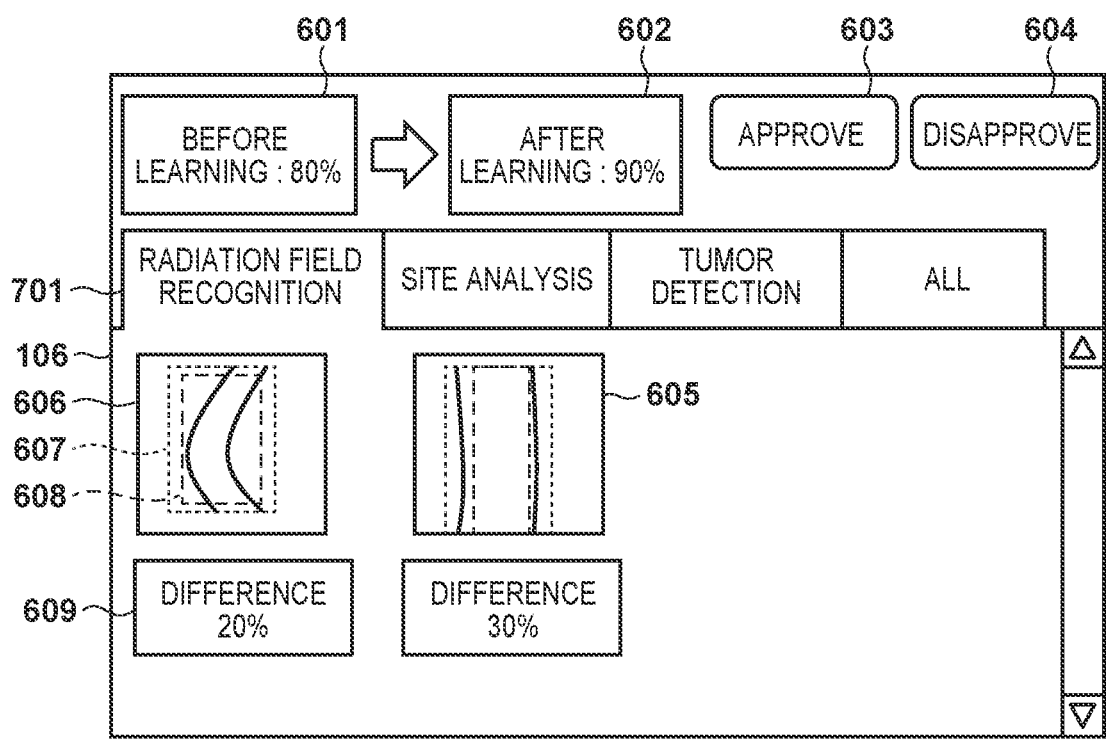
FIG. 7B is a diagram showing a variation of display appearance.

As shown in FIG. 7B, it is also possible to provide function selection for selecting a learning function in order to display evaluation results for a plurality of learning functions. In this case, the display unit 106 displays, for each teaming function, a medical image of a target determined as an incorrect answer in evaluation of a learning result performed by the evaluating unit 104, and the cause of it. Specifically, the display unit 106 displays, for each learning function, medical images determined as incorrect answers and difference information indicating the difference between the correct-answer data of the evaluation data held in the evaluation data holding unit 105 and the learning result of the learning unit 103.

Evaluation data is held in the evaluation data holding unit 105, according to each learning function such as radiation field recognition, site analysis, or tumor mass detection. The evaluating unit 104 associates a learning result of learning performed by the learning unit 103 with evaluation data held in the evaluation data holding unit 105. The learning result includes information regarding a learning function for which the learning unit 103 performed learning. For example, in the case of a learning result for radiation field recognition, evaluation data for radiation field recognition is extracted from the evaluation data holding unit 105, and is associated with the learning result of radiation field recognition. In the case of a learning result for site analysis, evaluation data for site analysis is extracted from the evaluation data holding unit 105, and is associated with the learning result for site analysis. In the case of a learning result for tumor mass extraction, evaluation data for tumor mass extraction is extracted from the evaluation data holding unit 105, and is associated with the learning result for tumor mass extraction.

The evaluating unit 104 evaluates a leaning result using evaluation data associated in accordance with the learning content, and extracts a medical image of a target determined as an incorrect answer and the cause of it. The display unit 106 can display a medical image of a target determined as an incorrect answer in evaluation of a learning result performed by the evaluating unit 104 and the cause of it, for each of radiation field recognition, site analysis, tumor mass extraction.

A function selection portion (function selection tag) 701 for selecting a function is displayed on the display unit 106. In the illustrated example, the user can select one of "radiation field recognition", "site analysis", "tumor mass detection", and "all" using the function selection portion 701. As a result of the user operating the function selection portion 701 to give an instruction on a learning function, a failure example for the learning function is displayed. For example, when the user selects radiation field recognition using the function selection portion 701, a medical image for radiation field recognition determined as an incorrect answer in evaluation of a learning result and the cause of it are displayed. With such a configuration, the user can efficiently confirm evaluation results for a plurality of learning functions, and perform validity examination.

Variation 2-3

According to Variation 2-3, the display unit 106 displays a processing result determined as an incorrect answer by the evaluating unit 104, for each type of imaging apparatus (modality).

Figure 8A:
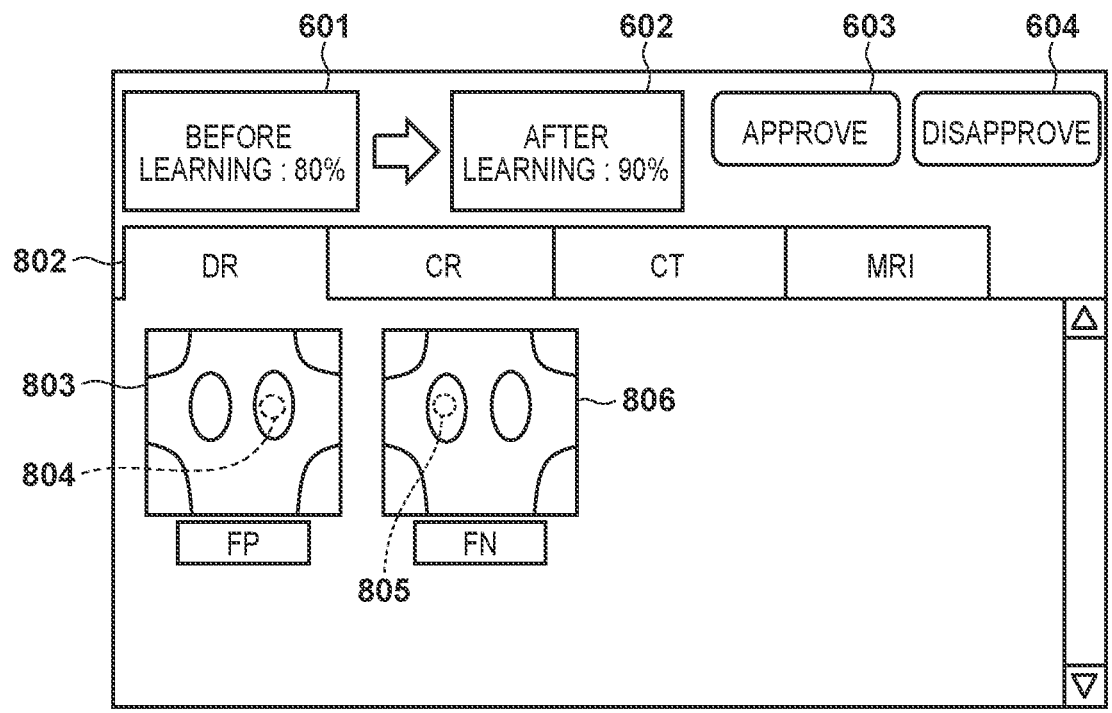
FIG. 8A is a diagram showing a variation of display appearance.

FIG. 8A shows a display example of the display unit 106 that can display an evaluation result for each type of a plurality of imaging apparatuses (for each modality). The display unit 106 displays, for each type of imaging apparatus, a medical image of a target determined as an incorrect answer in evaluation of a learning result performed by the evaluating unit 104 and the cause of it. Specifically, the display unit 106 displays, for each type of imaging apparatus, a medical image determined as an incorrect answer and difference information indicating the difference between the correct-answer data of evaluation data held in the evaluation data holding unit 105 and a learning result of the learning unit 103.

An imaging apparatus selection portion (imaging apparatus selection tag) 802 for selecting a type of imaging apparatus is displayed on the display unit 106. Here, "DR (Digital Radiography)", "CR (Computed Radiography)", "CT (Computed Tomography)", or "MRI (Magnetic Resonance Imaging)" can be selected using the imaging apparatus selection portion 802. As a result of the user operating the imaging apparatus selection portion 802, and giving an instruction on an imaging apparatus, a failure example for the imaging apparatus is displayed. For example, if the user selects DR using the imaging apparatus selection portion 802, a medical image for DR determined as an incorrect answer in evaluation of a learning result and the cause of it are displayed. Here, radiation images 803 and 806 are displayed on the display unit. For example, information 804 indicating the difference due to erroneous detection (normal site determined as being abnormal) in image recognition is displayed in the radiation image 803. On the other hand, in the radiation image 806, information 805 indicating an overlooked portion in image recognition (site to be detected as being abnormal (correct answer)) is displayed.

In this manner, the user can efficiently confirm an evaluation result for each type of a plurality of imaging apparatuses, and perform validity examination.

Variation 2-4

Figure 8B:
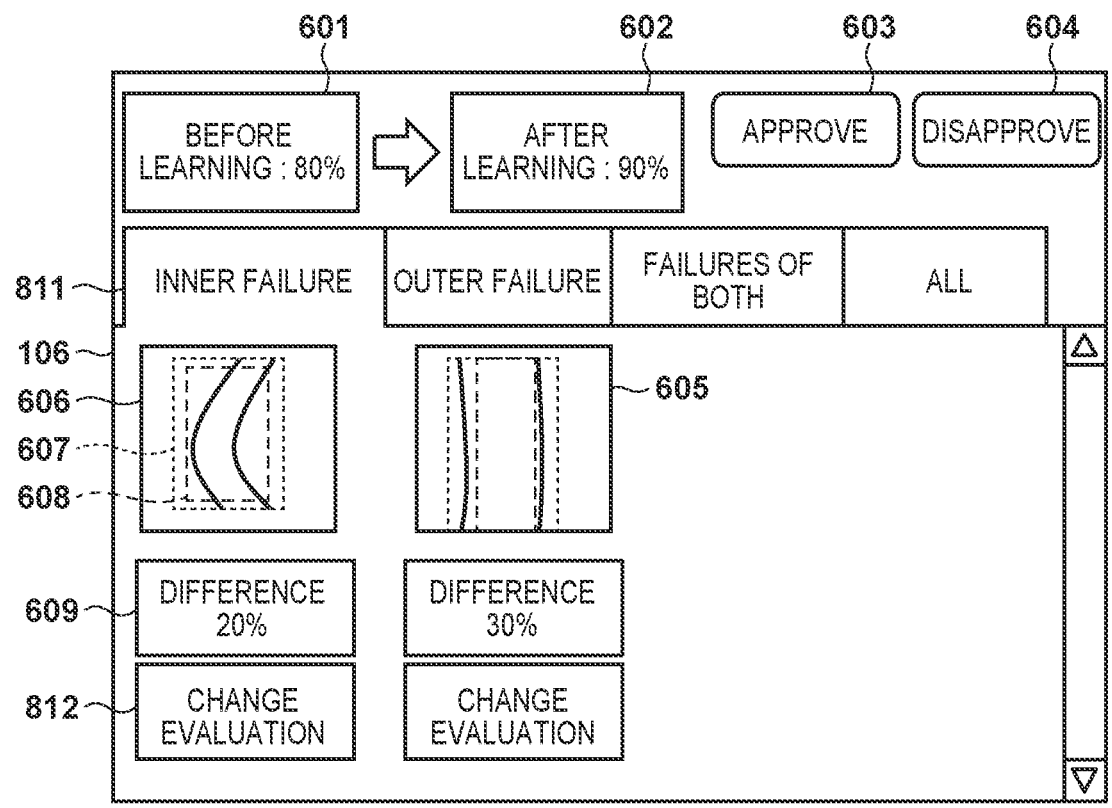
FIG. 8B is a diagram showing a variation of display appearance.

The display unit 106 according to Variation 2-4 displays a processing result determined as an incorrect answer by the evaluating unit 104, according to the category of the incorrect answer. FIG. 8B is a diagram showing an example of display of the display unit 106 according to Variation 2-4, and shows a display example of an evaluation result for radiation field analysis for each category of an incorrect answer.

The display unit 106 displays, for each category, a medical image of a target determined as an incorrect answer in evaluation of a learning result performed by the evaluating unit 104 and the cause of it. Specifically, the display unit 106 displays, for each category of failure, a medical image determined as an incorrect answer, difference information indicating the difference between correct-answer data of evaluation data held in the evaluation data holding unit 105 and a learning result of the learning unit 103. A category selection portion (category selection tag) 811 for selecting a category of failure is displayed on the display unit 106.

In this example, regarding a learning result for the radiation field region detection function, the user can select one of "inner failure", "outer failure", "both failures", and "all" using the category selection portion 811. As a result of the user performing an operation on the category selection portion 811 and giving an instruction on a category, a failure example for the category is displayed. "Inner failure" refers to a case where a boundary of a radiation field region has been detected on the inner side of the radiation field region of the correct answer. "Outer failure" refers to a case where a boundary of a radiation field region has been detected on the outer side of the radiation field region of the correct answer. "Both failures" refer to a case where there are a boundary portion detected on the outer side of the radiation field region of the correct answer and a boundary portion detected on the inner side. "All" refers to all the cases of an inner failure, an outer failure, and both failures.

FIG. 8B shows a display example of a case where the user selects "inner failure" using the category selection portion 811. When the user assumes that the degree of influence that a failure on the outer side has on clinical performance regarding detection of a radiation field region is higher than a failure on the inner side, the user can examine the validity by first confirming an example of a failure on the inner side only, for example.

In addition, the display unit 106 according to Variation 2-4 includes a change portion (not illustrated) that changes, to a correct answer, determination on a processing result selected from processing results determined as incorrect answers by the evaluating unit 104. In FIG. 8B, as an example of the change portion, an evaluation change setting portion 812 is provided below a failure image. The user can change an evaluation result using the evaluation change setting portion 812. For example, even in a case regarded as a failure in terms of a numerical value, when clinical performance is not affected, the user can change the evaluation.

As described above, the validity can be efficiently examined by displaying failure examples for each failure category. In addition, also regarding picking up of failure examples, which has been described in the second embodiment, it is possible to perform confirmation evenly in terms of failure categories by picking up failure examples for each failure category.

Note that, in Variation 2-4, a display example of evaluation results for radiation field recognition have been described, but it is needless to say that the present invention is also applicable to evaluation result display for another function. For example, category classification according to whether detection of tumor mass indicates false positive or false negative is conceivable. In addition, in the case of a function for preferences in image quality, category classifications according to whether or not the difference in contrast is large, whether or not the difference in noise is large, and the like are conceivable.

Variation 2-5

In Variation 2-5, the evaluating unit 104 obtains the difference between a processing result obtained by processing target data included in evaluation data for a function after learning and correct-answer data included in the evaluation data, and determines whether or not the processing result is a correct answer or an incorrect answer, based on the difference. The display unit 106 displays, on the display device, a processing result along with correct-answer data of corresponding evaluation data, for each mode of a change in evaluation (determination) performed by the evaluating unit 104 before and after learning.

Figure 9A:
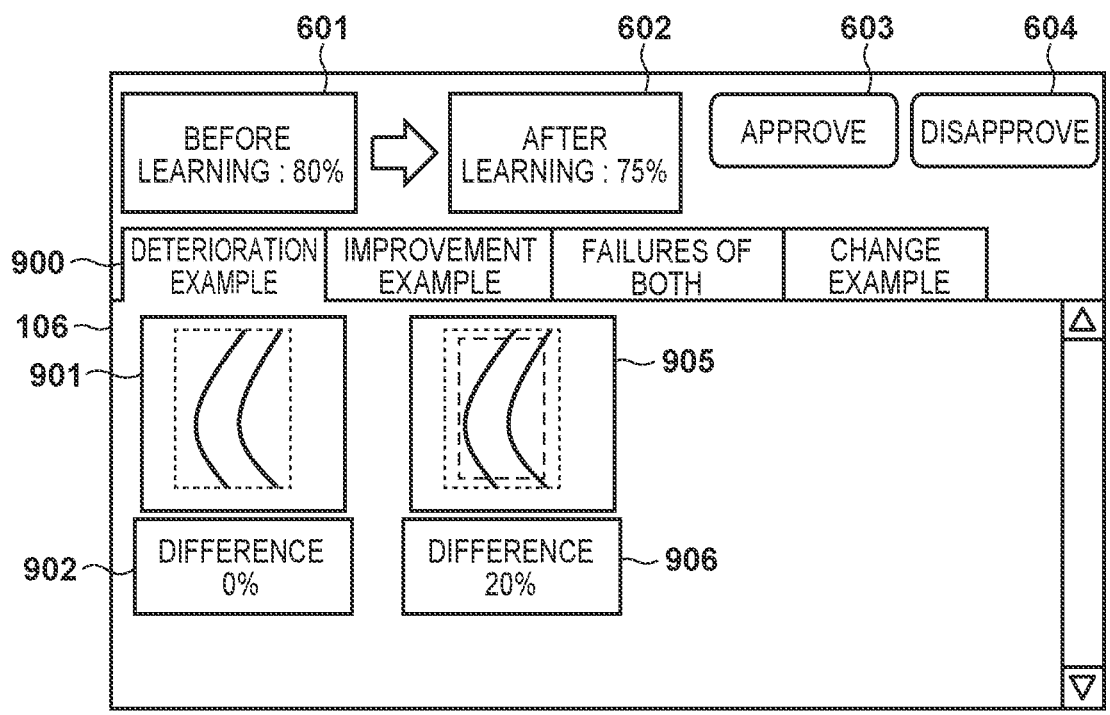
FIG. 9A is a diagram showing a variation of display appearance.

As shown in FIG. 9A, it is possible to display a case where there is a change before and after learning. The display unit 106 displays a case where there was a change before and after learning, along with a medical image. Specifically, the display unit 106 displays a case of deterioration after learning, a case of improvement after learning, a case of failures both before and after learning, and another change example along with a medical image. The display unit 106 displays a change mode selection portion (change mode selection tag) 900 for selecting a case where there is a change before and after learning. The user can select one of "deterioration example", "improvement example", "example of both failures", and "change example", using the change mode selection portion 900, "Deterioration example" refers to a case where a correct answer before learning changed to an incorrect answer after learning. "improvement example" refers to a case where an incorrect answer before learning changed to a correct answer after learning. "Example of both failures" refers to a case where an incorrect answer before learning remains an incorrect answer after learning. "Change example" refers to a combination of a deterioration example and an improvement example (a change from a correct answer to an incorrect answer through learning and a change from an incorrect answer to a correct answer).

FIG. 9A shows a state where "deterioration example" is selected. The display unit 106 displays a medical image 901 and difference information 902 before learning. The difference information 902 indicates the difference between correct-answer data of evaluation data held in the evaluation data holding unit 105 and a learning result before the learning unit 103 performs learning. In addition, the display unit 106 displays a medical image 905 after learning and difference information 906. The difference information 906 indicates the difference between correct-answer data of evaluation data held in the evaluation data holding unit 105 and a learning result after the learning unit 103 has performed learning. In this manner, the user can recognize that, based on a change in the difference that is being displayed on the display unit 106, the difference information 906 after learning has deteriorated relative to the difference information 902 before learning.

As described above, according to Variation 2-5, a change in performance due to learning can be confirmed in terms of not only numerical values but also individual cases, and thus the user can easily examine the validity.

Variation 2-6

In Variation 2-6, a description will be given on the display unit 106 that displays processing results determined as incorrect answers by the evaluating unit 104, for each of the types of learning for which different learning data is used.

Figure 9B:
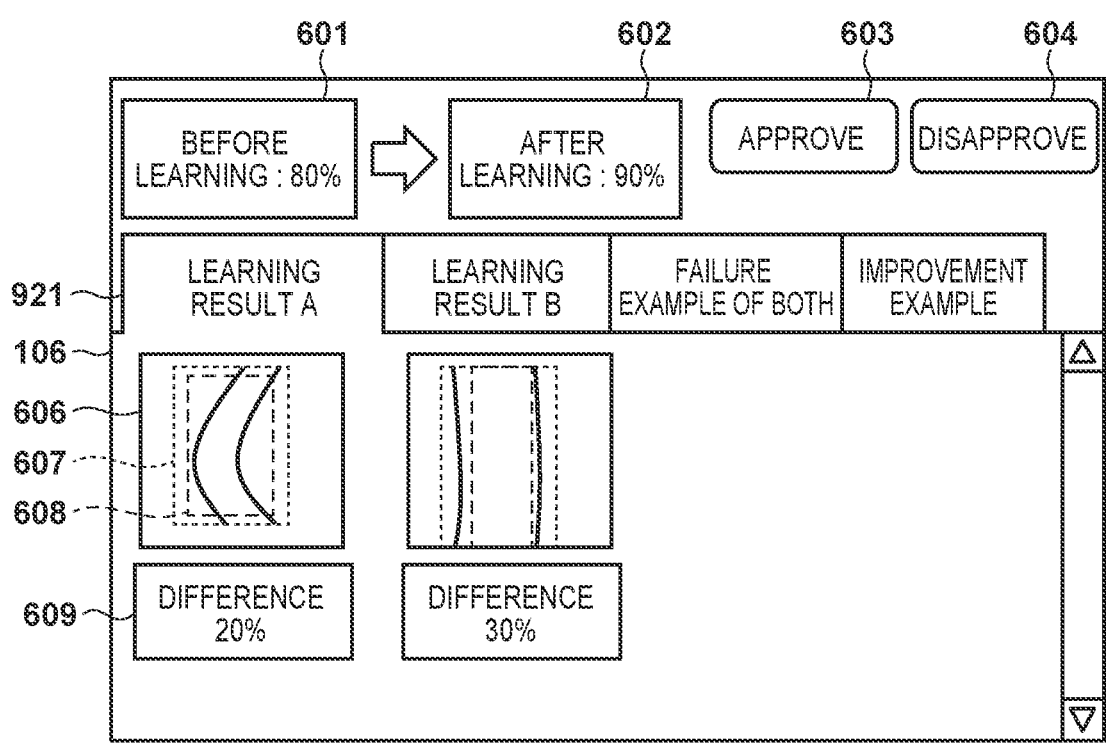
FIG. 9B is a diagram showing a variation of display appearance.

As shown in FIG. 9B, the display unit 106 can display a plurality of learning results using different types of learning data for the same function. In the example in FIG. 9B, the user can select one of "learning result A", "learning result B", "failure examples of both", and "change example" using a learning result selection portion 921. In accordance with one of "learning result A" and "learning result B" being selected, a failure example of one of the two learning results, namely the learning result A and the learning result B is displayed. In accordance with "failure examples of both" being selected, an example is displayed in which both the learning results A and B indicate a failure. In addition, in accordance with "change example" being selected, an example is displayed in which the learning result A and the learning result B indicate different results (data for which a processing result is determined as a correct answer due to one type of learning and a processing result is determined as an incorrect answer due to another type of learning).

As described above, according to Variations 2 to 6, when there are two learning results, the user can confirm evaluation results and failure image examples for the two results, perform validity examination, and select and approve one of the learning results. By using this variation, the user can efficiently select a learning result for which clinically demanded performance is higher.

Variation 2-7

Figure 10:
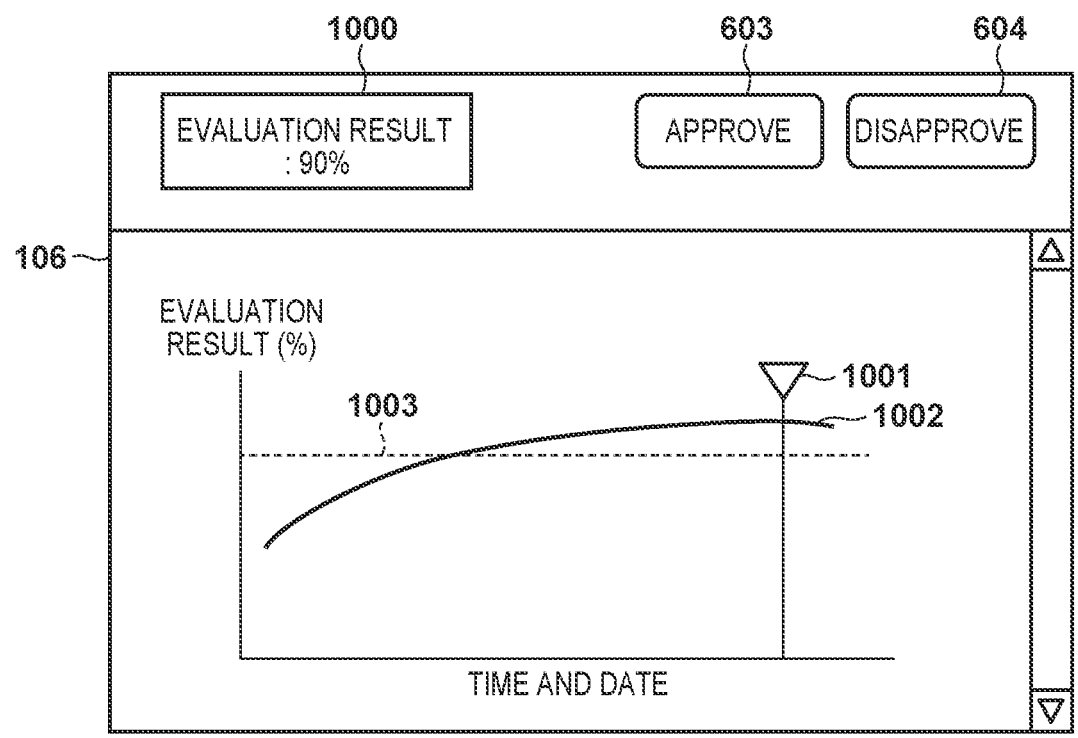
FIG. 10 is a diagram showing a variation of display appearance.

While results before and after learning are displayed according to the second embodiment and above variations, the display unit 106 according to Variation 2-7 displays a temporal change of an evaluation result (correct answer ratio) as shown in FIG. 10. In this manner, the display unit 106 according to Variation 2-7 displays an evaluation result of machine learning evaluated by the evaluating unit 104, along with time information. For example, the display unit 106 displays an evaluation result as a graph in which a first axis indicates value of an evaluation result and a second axis indicates time.

In the display example in FIG. 10, the display unit 106 displays a change 1002 of an evaluation result of machine learning evaluated by the evaluating unit 104 along with time information (time and date). In the example shown in FIG. 10, the user can recognize that evaluation of machine learning has improved than before, by referring to the change 1002 of the evaluation result of machine learning. The user confirms the evaluation result of machine learning, and presses the approval portion 603 or the disapproval portion 604 so as to select approval or disapproval.

The most recent learning result is not necessarily most highly evaluated. Therefore, the user confirms an evaluation result of machine learning corresponding to a desired time (time and date), and approves the learning result. Specifically, the user can set a time designation cursor 1001 on the change 1002 of the evaluation result of machine learning. The display unit 106 can display an evaluation result 1000 of machine learning corresponding to the time (time and date) designated by the time designation cursor 1001. The user can confirm the evaluation result 1000 of machine learning corresponding to the time (time and date) designated using the time designation cursor 1001, and press the approval portion 603 or the disapproval portion 604 so as to select approval or disapproval. As a result of the user referencing the change 1002 of the evaluation result of machine learning, and designating, using the time designation cursor 1001, a time (time and date) when learning is most highly evaluated, the user can achieve the learning state of machine learning for which the evaluation result is the highest.

In addition, as a result of the change 1002 of the evaluation result of machine learning being analyzed by an analysis unit (not illustrated), a time (time and date) when evaluation is the highest being detected, and the time (time and date) being designated, it is possible to achieve the learning state of machine learning for which the evaluation result is the highest.

The display unit 106 can also display an evaluation index value (evaluation threshold value) 1003 that is a criterion for approving a learning result. When the evaluation result 1000 of machine learning corresponding to the time (time and date) designated by the time designation cursor 1001 exceeds the evaluation index value (evaluation threshold value) 1003, the user can approve the learning result using the approval portion 603. A configuration may also be adopted in which, if the evaluation result 1000 of machine learning corresponding to the time (time and date) designed using the time designation cursor 1001 does not exceed the evaluation index value (evaluation threshold value) 1003, only the disapproval portion 604 can be pressed. In this case, it is possible to impose restriction on the approval portion 603 such that the learning result cannot be approved.

As described above, as a result of the graph of an evaluation result being displayed, the user can confirm the speed of the improvement of performance obtained through learning and the limit for improvement of performance, and the displayed evaluation result is used as an index for examining the validity.

Third Embodiment

Figure 11:
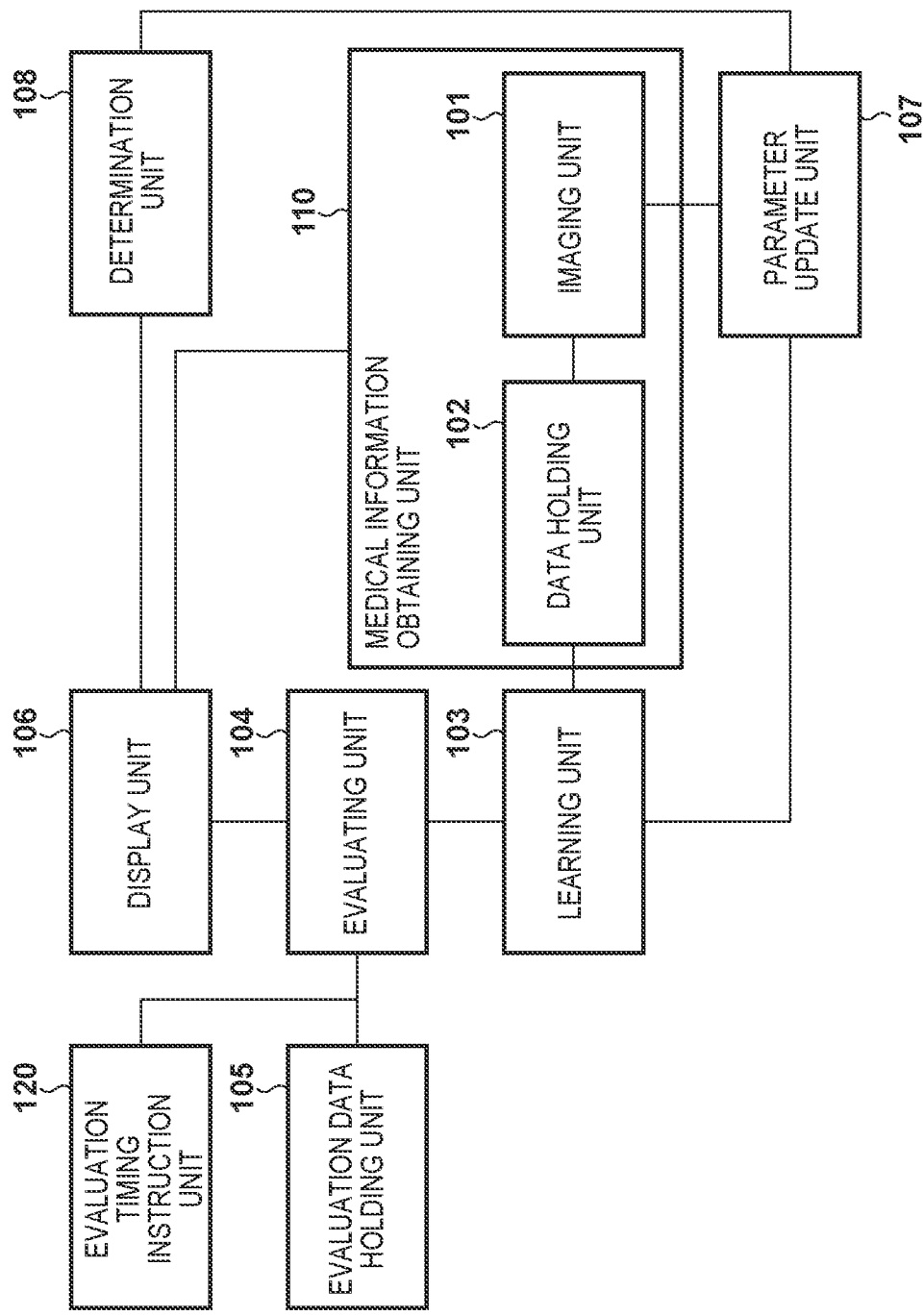
FIG. 11 is a diagram showing an exemplary function configuration of a medical information processing apparatus according to a third embodiment.

In a third embodiment, a description will be given on a medical information processing apparatus provided with an instruction unit for giving an instruction on a timing for the evaluating unit 104 to start evaluation. FIG. 11 is a block diagram showing an exemplary function configuration of the medical information processing apparatus according to the third embodiment. The same reference signs are assigned to function units that are similar to the first embodiment (FIG. 1). According to the third embodiment, an evaluation timing instruction unit 120 is provided. The evaluation timing instruction unit 120 gives an instruction on an execution timing of performance evaluation (step S204 in FIG. 2).

Figure 12:
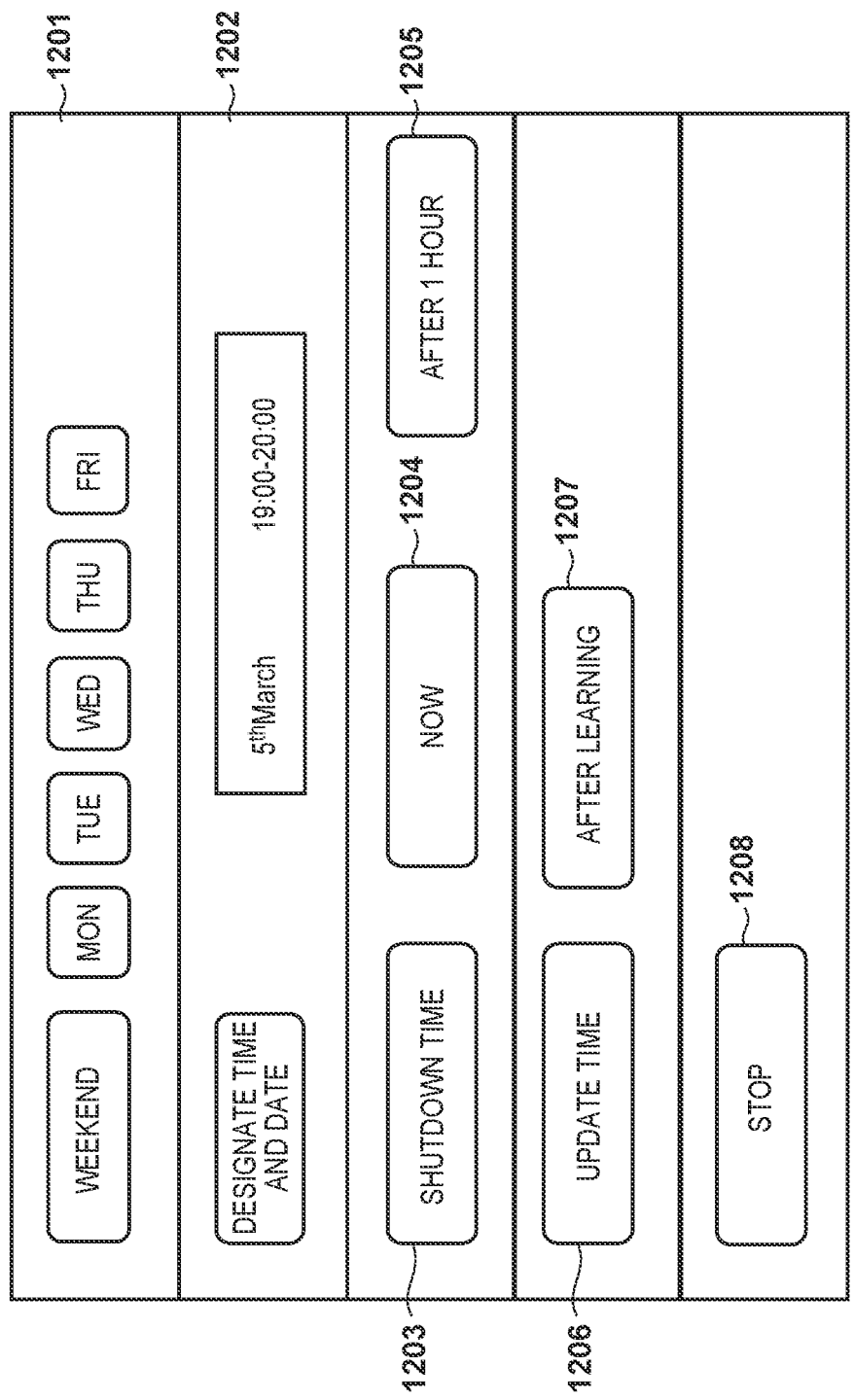
FIG. 12 is a diagram showing an example of display appearance of a display unit according to the third embodiment.

Next, an instruction method that is performed by the evaluation timing instruction unit 120 will be described. According to the third embodiment, the evaluation timing instruction unit 120 can give an instruction a plurality of different evaluation timings. FIG. 12 shows an example of the evaluation timing instruction unit 120. In the example in FIG. 12, the user can operate the evaluation timing instruction unit 120 and give an instruction on an evaluation timing. When the user selects one of the day-of-the-week select buttons 1201 in FIG. 12, an instruction to carry out evaluation on the selected day of the week is given. As a result of selecting a day of the week, evaluation can be carried out at a tinning when there is no clinic practice and the imaging system is not used, for example. In addition, when the user selects a time-and-date designation button 1202, the user can give an instruction on any evaluation timing. The user can carry out evaluation in accordance with circumstances by designating a time and date.

In addition, when the user selects a "at the time of shutdown" select button 1203, evaluation can be performed when the imaging system is shut down. This makes it possible to carry out evaluation, for example, when it is known that the imaging system is not to be used for a while after shutdown. In addition, when the user selects a "now" select button 1204, evaluation is promptly carried out. When it is desired to promptly perform validity evaluation, evaluation can be carried out promptly. In addition, when the user selects a "one hour after" select button 1205, evaluation is carried out in an hour after the selection. For example, when it is known in advance that imaging that is performed by the imaging system will end in an hour, evaluation can be performed at that timing.

In addition, if the user selects an "at the time of update" select button 1206, evaluation is carried out at the timing when evaluation data is updated. For example, when evaluation data is updated to data obtained by the imaging system in this medical information system, or evaluation data is updated to new evaluation data, evaluation can be promptly performed using the new data. In addition, when the user selects an "after learning" select button 1207, evaluation is carried out at a timing after machine learning. With such a configuration, the user can perform validity examination promptly after machine learning.

Note that, according to the third embodiment, a case has been described in which various selections are used individually, but it is also possible to use timings in combination. For example, a configuration can be adopted in which, as a result of combining the day-of-the-week select button 1201 and the "after learning" select button 1207, evaluation is carried out on the selected day of the week that comes first after learning is performed. This is represented by AND of evaluation start conditions. In addition, timings can be combined when both evaluation to be performed promptly after learning and evaluation to be performed on a designated day of every week are valid. This is represented by OR of evaluation start conditions. Combining timings in this manner enables more appropriate scheduling for examining the validity based on operations of the medical information system.

In addition, when the user selects a stop button 1208 in FIG. 12, the user can stop evaluation that is currently performed. For example, when the medical information system is desired to be used while evaluation is being performed, it is possible to reduce the load on the medical information system by stopping the evaluation.

As described above, according to the third embodiment, as a result of using the medical information system provided with the evaluation timing instruction unit 120, it is possible to perform load adjustment for evaluation, and perform evaluation at an appropriate timing for performing validity examination.

According to the above-described embodiments, a user can appropriately determine whether or not a learning result can be applied, based on a result of examining the validity of learning, in a medical information processing apparatus.

Other Embodiments

Embodiment(s) of the present invention can also be realized by a computer of a system or apparatus that reads out and executes computer executable instructions (e.g., one or more programs recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A medical information processing apparatus, comprising:
   at least one of (a) one or more processors connected to one or more memories storing a program including instructions executed by the one or more processors and (b) circuitry configured to perform:

obtaining medical information;
learning on a function of the medical information processing apparatus using the medical information, wherein the learning is performed for at least one of image recognition in which region information is obtained as a result of processing by the function, image processing in which an image processing condition is obtained as a result of processing by the function, and diagnostic support in which lesion position information is obtained as a result of processing by the function;
evaluating a learning result obtained through learning on at least one of the image recognition, the image processing, and the diagnostic support using a comparison result obtained by comparing, for each corresponding pixel, a result obtained by processing a medical image included in an evaluation data, wherein the evaluation date is for evaluating the learning result by the learning, and the evaluation data includes the medical image and the correct-answer data in which a correct answer for at least one of the image recognition, the image processing, and the diagnostic support is known; and
accepting an instruction to apply the learning result to the function.

2. The medical information processing apparatus according to claim 1, wherein the at least one of (a) one or more processors and (b) circuitry is configured to further perform:
changing determination of a selected processing result from among processing results determined as incorrect answers by the evaluating, to a correct answer.

3. The medical information processing apparatus according to claim 1, wherein the at least one of (a) one or more processors and (b) circuitry is configured to further perform:
giving an instruction on a timing for the evaluating to start evaluation.

4. The medical information processing apparatus according to claim 1, wherein in the evaluating, the learning result is evaluated based on evaluation data relating to any one of the image recognition, the image processing, and the diagnostic support selected according to a type of the function.

5. The medical information processing apparatus according to claim 1, the correct data included in the evaluation data for the image recognition includes at least one of an irradiation field region, an anatomical region, and a lesion region as the region information.

6. The medical information processing apparatus according to claim 1, wherein the correct-answer data regarding the image processing included in the evaluation data includes at least one of a tone processing condition and a noise processing condition as the image processing condition.

7. The medical information processing apparatus according to claim 1, in the evaluating, the learning result is evaluated using a matching rate obtained using the number of mutually matching pixels or the number of non-matching pixels obtained by comparing the corresponding pixels.

8. A medical information processing apparatus comprising:
at least one of (a) one or more processors connected to one or more memories storing a program including instructions executed by the one or more processors and (b) circuitry configured to perform:
obtaining medical information;
learning on a function of the medical information processing apparatus using the medical information, wherein the learning is performed for at least one of image recognition in which region information is obtained as a result of processing by the function, image processing in which an image processing condition is obtained as a result of processing by the function, and diagnostic support in which lesion position information is obtained as a result of processing by the function;
evaluating a learning result obtained through learning on at least one of the image recognition, the image processing, and the diagnostic support using a comparison result obtained by comparing, for each corresponding pixel, a result obtained by processing a medical image included in an evaluation data, wherein the evaluation date is for evaluating the learning result by the learning, and the evaluation data includes the medical image and the correct-answer data in which a correct answer for at least one of the image recognition, the image processing, and the diagnostic support is known; and
controlling a display device to display a result of the evaluation along with a change in the function caused by the learning.

9. The medical information processing apparatus according to claim 8, wherein the at least one of (a) one or more processors and (b) circuitry is configured to further perform:
accepting a user's instruction to apply a learning result of the learning to the function.

10. The medical information processing apparatus according to claim 8,
wherein in the controlling the display device, evaluation results obtained by the evaluating before and after the learning are displayed.

11. The medical information processing apparatus according to claim 10,
wherein the evaluation results indicate a ratio of evaluation data determined as a correct answer based on a result of the comparison or a ratio of evaluation data determined as an incorrect answer based on a result of the comparison.

12. The medical information processing apparatus according to claim 8,
wherein in the evaluating, a difference between correct-answer data included in the evaluation data and a processing result obtained by processing a medical image included in the evaluation data using the learning result is obtained based on the comparison result, and determines whether or not the processing result is an incorrect answer based on the difference, and
wherein in the controlling the display device, a processing result determined as an incorrect answer by the evaluating unit and correct-answer data of corresponding evaluation data.

13. The medical information processing apparatus according to claim 12,
wherein in the controlling the display device, a processing result determined as an incorrect answer by the evaluating and correct-answer data of corresponding evaluation data are superimposed over a medical image of the corresponding evaluation data.

14. The medical information processing apparatus according to claim 12,
wherein in the controlling the display device, difference information indicating the difference related to a processing result determined as an incorrect answer by the evaluating.

15. The medical information processing apparatus according to claim 12, wherein the at least one of (a) one or more processors and (b) circuitry is configured to further perform:
setting a range of difference, wherein in the controlling the display device, a processing result for which a difference obtained by the evaluating is within the range is displayed.

16. The medical information processing apparatus according to claim 12,
wherein in the controlling the display device, a processing result determined as an incorrect answer by the evaluating is displayed by the at least one of a display, a display for each type of function for which learning has been performed, a display for each type of imaging apparatus, a display for each mode of difference and display for each type of learning for which learning data is different.

17. A medical information processing method, comprising:
obtaining medical information;
performing learning on a function of a medical information processing apparatus using the medical information, wherein the learning is performed for at least one of image recognition in which region information is obtained as a result of processing by the function, image processing in which an image processing condition is obtained as a result of processing by the function, and diagnostic support in which lesion position information is obtained as a result of processing by the function;
evaluating a learning result obtained through learning on at least one of the image recognition, the image processing, and the diagnostic support using a result obtained by comparing, for each corresponding pixel, a result obtained by processing a medical image included in an evaluation data using the learning result and a correct-answer data included in the evaluation data, wherein the evaluation data is for evaluating the learning result by the learning, and the evaluation data includes the medical image and the correct-answer data in which a correct answer for at least one of the image recognition, the image processing, and the diagnostic support is known; and
accepting an instruction to apply the learning result in the learning to the function.

18. A medical information processing method, comprising:
obtaining medical information;
performing learning on a function of a medical information processing apparatus using the medical information, wherein the learning is performed for at least one of image recognition in which region information is obtained as a result of processing by the function, image processing in which an image processing condition is obtained as a result of processing by the function, and diagnostic support in which lesion position information is obtained as a result of processing by the function;
evaluating a learning result obtained through learning on at least one of the image recognition, the image processing, and the diagnostic support using a result obtained by comparing, for each corresponding pixel, a result obtained by processing a medical image included in an evaluation data using the learning result and a correct-answer data included in the evaluation data, wherein the evaluation data is for evaluating the learning result by the learning, and the evaluation data includes the medical image and the correct-answer data in which a correct answer for at least one of the image recognition, the image processing, and the diagnostic support is known; and
displaying, on a display device, a result of the evaluation along with a change caused by the learning.

19. A non-transitory computer-readable storage medium storing a program for causing a computer to execute a medical information processing method comprising:
obtaining medical information;
performing learning on a function of a medical information processing apparatus using the medical information, wherein the learning is performed for at least one of image recognition in which region information is obtained as a result of processing by the function, image processing in which an image processing condition is obtained as a result of processing by the function, and diagnostic support in which lesion position information is obtained as a result of processing by the function;
evaluating a learning result obtained through learning on at least one of the image recognition, the image processing, and the diagnostic support using a result obtained by comparing, for each corresponding pixel, a result obtained by processing a medical image included in an evaluation data using the learning result and a correct-answer data included in the evaluation data, wherein the evaluation data is for evaluating the learning result by the learning, and the evaluation data includes the medical image and the correct-answer data in which a correct answer for at least one of the image recognition, the image processing, and the diagnostic support is known; and
accepting an instruction to apply a learning result in the learning to the function.

20. A non-transitory computer-readable storage medium storing a program for causing a computer to execute a medical information processing method comprising:
obtaining medical information;
performing learning on a function of a medical information processing apparatus using the medical information, wherein the learning is performed for at least one of image recognition in which region information is obtained as a result of processing by the function, image processing in which an image processing condition is obtained as a result of processing by the function, and diagnostic support in which lesion position information is obtained as a result of processing by the function;
evaluating a learning result obtained through learning on at least one of the image recognition, the image processing, and the diagnostic support using a result obtained by comparing, for each corresponding pixel, a result obtained by processing a medical image included in an evaluation data using the learning result and a correct-answer data included in the evaluation data, wherein the evaluation data is for evaluating the learning result by the learning, and the evaluation data includes the medical image and the correct-answer data in which a correct answer for at least one of the image recognition, the image processing, and the diagnostic support is known; and
displaying, on a display device, a result of the evaluation along with a change caused by the learning.

* * * * *